(12) United States Patent
Giannini et al.

(10) Patent No.: US 7,084,166 B2
(45) Date of Patent: Aug. 1, 2006

(54) BIS-HETEROCYCLIC COMPOUNDS WITH ANTITUMOUR AND CHEMOSENSITISING ACTIVITY

(75) Inventors: Giuseppe Giannini, Rome (IT); Mauro Marzi, Rome (IT); Maria Ornella Tinti, Rome (IT); Claudio Pisano, Rome (IT); Gian Piero Moretti, Rome (IT); Patrizia Minetti, Rome (IT); Enrico Garattini, Milan (IT); Sergio Penco, Milan (IT)

(73) Assignee: Sigma-Tau Industrie Farmaceutichee Riunite S.p.A., Rome (IT)

( * ) Notice: Subject to any disclaimer, the term of this patent is extended or adjusted under 35 U.S.C. 154(b) by 165 days.

(21) Appl. No.: 10/415,898

(22) PCT Filed: Jul. 26, 2001

(86) PCT No.: PCT/IT01/00407

§ 371 (c)(1),
(2), (4) Date: Sep. 9, 2003

(87) PCT Pub. No.: WO02/36561

PCT Pub. Date: May 10, 2002

(65) Prior Publication Data

US 2004/0053987 A1 Mar. 18, 2004

(30) Foreign Application Priority Data

Nov. 3, 2000 (IT) .......................... RM2000A0569

(51) Int. Cl.
*A61K 31/404* (2006.01)
*C07D 209/08* (2006.01)

(52) U.S. Cl. ........................................ 514/414; 548/455
(58) Field of Classification Search ................ 548/455; 514/414
See application file for complete search history.

(56) References Cited

U.S. PATENT DOCUMENTS 4,897,494 A * 1/1990 Psaar et al. .................. 548/455

FOREIGN PATENT DOCUMENTS

| EP | 0 887 348 A | 12/1998 |
| WO | 95/08540 A | 3/1995 |

OTHER PUBLICATIONS

Bergman, "Reactions of Indoles ith Ortho Esters, N,N-Dimethylformamide and N,N-Dimethylacetamide Dialkyl Acetals," J. Heterocyclic Chem., vol. 22, Issue 2, pp. 341-343 (1985).*
Uile F C et al; "The Synthesis and Cyclization of Alpha-Methylamino-Beta-(4-Carboxy-3-Indole)-Propionic Acid"; Journal of the American Chemical Society, American Chemical Society, Washington, DC, US, vol. 79, Jan. 5, 1957, pp. 102-119, XP001022584.
Snyder H R et al; "Carbon Alkylations With 1-Methylgramine and Its Methiodide"; Journal of the American Chemical Society, American Chemical Society, Washington, DC, US, Feb. 1949, pp. 663-669, XP001022629.
Brown R K et al; "Derivatives of Indole, 6-Amino-3-Indoleacetic Acid"; Journal of the American Chemical Society, XX, XX,; Jul. 20, 1955, pp. 3839-3842, XP001022633.
Ananthanarayanan C V et al; "3,4-Bridged Indoles: Part 11-Synthesis of 6-Keto-I, 5-Dihydro-4, 5-Diazepinoa6, 5, 4-Cduindoles & 3, 4-Disubstituted Indoles as 5-HT Antagonists"; Indian Journal of Chemistry, Jodhpur, IN, vol. 158, Aug. 1977, pp. 710-714, XP001022623.
A Kamal; "Syntheses of Some Substituted Di-Indolylmethanes"; Tetrahedron, vol. 19, 1963, pp. 513-520, XP001022583.
H Hellmann; "Synthesen Mit Tertiaren Mannich-Basen, IX"; Chemische Berichte, vol. 87, 1954, pp. 940-945, XP001022585.
Bergman J et al; "Conversion of Diindolyl Methanes to 3-Vinylindoles a Simple Synthesis of the Indole Alkaloid Olivacine"; Tetrahedron Letters, Elsevier Science Publishers, Amsterdam, NL, No. 42, 1978, pp. 4055-4058, XP001022777.
Bergman J; "Reactions of Indole With Ortho Esters, N,N-Dimethylformanmide and N,N-Dimethylacetamide Dialkyl Acetals"; Journal of Heterocyclic Chemistry, Heterocorporation, Provo, US, vol. 22, No. 341, Mar. 1985, pp. 341-343, XP001022743.
Bergman J et al; "Synthesis of 1-(2-Ethyl-3-Indolyl)-1-(3-Pyridyl)Ehtylen E and Related Ellipticine Analogues"; Journal of Heterocyclic Chemistry, Heterocorporation. Provo, US, vol. 22, Aug. 1972, pp. 833-836, XP001022741.

* cited by examiner

*Primary Examiner*—Kamal A. Saeed
*Assistant Examiner*—Andrew B. Freistein
(74) *Attorney, Agent, or Firm*—Nixon & Vanderhye P.C.

(57) ABSTRACT

Bis-heterocyclic compounds of general formula (I) are described which are useful as antitumour and cheomsensitising agents.

2 Claims, 4 Drawing Sheets

BIS-HETEROCYCLIC COMPOUNDS WITH ANTITUMOUR AND CHEMOSENSITISING ACTIVITY

Figure 1:
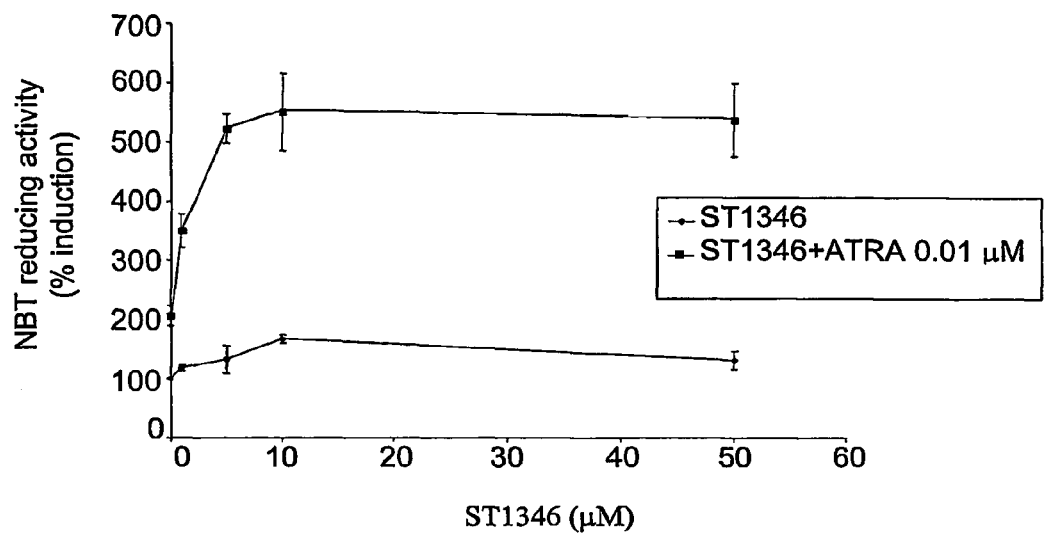

This application is a § 371 of PCT/IT01/00407, filed Jul. 26, 2001 and claims benefit of Italian Patent Application No. RM2000A000569, filed Nov. 3, 2000.

The invention described herein relates to bis-heterocyclic compounds of general formula (I) with antitumour and/or chemosensitising activity

(I)

where:

A, which may be the same as or different from A', is a mono- or bicyclic system with 5–7 atoms containing one or more atoms selected from N, S, O in one or both cycles;

A and A' can be bound to C—X in a symmetric or asymmetric manner;

X, which may be the same as or different from X', represents:

a) H, OH, X and X' together are: =O, =CH—$(CH_2)_nCH_3$ in which n is an integer ranging from 1 to 3;

b) a saturated or unsaturated straight or branched alkyl $C_1$–$C_{18}$ chain possibly substituted with: 1) cycloalkyl $C_3$–$C_7$; 2) $NR_1R_2$ in which $R_1$ and $R_2$, which may be the same or different, may be H, straight or branched alkyl $C_1$–$C_5$; 3) azide; 4) halogen; 5) one or more $OR_3$ groups in which $R_3$ represents H, straight or branched acyl $C_1$–$C_5$, or mesyl, tosyl, triflyl or, together with a vicinal OH, $R_3$ represents isopropylidene; 6) phenyl, in turn substituted with halogens, nitro, hydroxyl, alkoxy, or amino $NR_1R_2$ in which $R_1$ and $R_2$ have the meanings described above; 7) free or esterified carboxyl with straight and branched alkyls with 1 to 5 carbon atoms; 8) morpholin or methoxymorpholin;

c) cycloalkyl $C_3$–$C_7$;

d) phenyl or naphthyl, possibly substituted with halogen, nitro, hydroxyl, alkoxy, or amino $NR_1R_2$ groups in which $R_1$ and $R_2$ have the meanings defined above;

e) heterocycle $C_5$–$C_7$, possibly substituted with a halogen, nitro, hydroxyl, alkoxy, or amino $NR_1R_2$ group in which $R_1$, $R_2$ have the meanings defined above;

f) saturated heterocycle containing one or more heteroatoms selected from N, O, possibly substituted with OH, CN, O-alkyl $C_1$–$C_4$;

with the proviso that when A=A1=indole, X=H X' is not heterocyclic or phenyl or alkyl;

in which R, which may be the same as or different from R', represents H, hydroxyl, possibly esterified with acyls $C_1$–$C_4$, methylenedioxy, nitro, amino, possibly mono or alkylated $C_1$–$C_4$, mono or dialkanoyl $C_1$–$C_4$, carboxy, alkyloxycarbonyl, halogen, alkyl $C_1$–$C_4$;

if A and A', which may be the same or different, contain a nitrogen atom, this may be benzylated or alkylated $C_1$–$C_6$;

if A and A', which may be the same or different, contain an S atom, this may be oxidised in one of the two cycles.

The use of antineoplastic drugs in human therapy causes a substantial number of toxic or side effects which consequently lead to a reduction of the amount of drug to be administered, and in some cases to discontinuation of the therapy. A reduction of the amount of drug to be administered or discontinuation of the therapy cause an increase in primary tumour growth and/or the occurrence of tumour metastases. Clearly, in these cases the number of patients who die of cancer inevitably increases.

Another very important and keenly perceived aspect of oncological therapy is the onset of resistance to the drug used by the tumour cells treated. The cells that develop resistance to a drug are often capable of resisting the effects of many other antitumour drugs, even if these are unrelated chemically or act with different mechanisms of action. This type of resistance is called multidrug resistance (MDR) (Annu. Rev. Med 1991, 42: 277–286; Drugs of the Future 1997, 22: 653–660).

A number of tumours, such as, for instance, tumours of the adrenal cortex, colon, kidneys and jejunum and liver carcinoma manifest drug resistance right from the very start of treatment with antitumour drugs (Barrows, L. R. Antineoplastic and Immunoactive Drugs, 1995; 75; 1236–1262).

In other cases, the tumour cells acquire resistance in a manner similar to that of bacterial resistance to antibiotics. This type of resistance is based on genetic changes that occur in the tumour cells during treatment; these changes allow the daughter cells to proliferate in a milieu in which the antitumour agent is present.

Be that as it may, whatever the cause of the resistance, it leads to inefficacy of the antineoplastic treatment.

A number of studies suggest that a common form of drug resistance in human tumours derives from the presence of glycoprotein P (Ann. Med. Interna 1997 March; 14(3): 145–53; Acta Scient Venez. 2000;51(1):45–52)

This glycoprotein acts as an energy-dependent membrane pump which expels the antitumour drug from the interior of the cell, thus reducing the cellular concentratioon of the drug.

Chemosensitisers are compounds that bring about changes in tumour cells or in the body and favour an increase in the therapeutic efficacy of the antitumour agents used.

Chemosensitisers known to be capable of modulating the function of glycoprotein P include calcium-channel blockers (verapamil), calmodulin inhibitors (trifluoperazine), indole alkaloids (reserpine), lysosomotropic agents (chloroquin), steroids, (progesterone), triparanol analogues (tamoxifen), detergents (cremophor EL), and cyclic peptide antibiotics (cyclosporins) (Cancer, Principles & Practice of Oncology, 1993; 4th ed., J.B. Lippincott Co., Philadephia, Pa., 2661-2664).

Compounds with a bis-heterocyclic structure are already known. For example, WO 95/08540 describes bis-(amidinobenz-imidazolyl)alcans with antiviral activity.

WO 99/00381 describes bis-indole derivatives with antimetastatic activity.

U.S. Pat. No. 5,780,461 describes bis-indole derivatives with antitumour activity.

The bis-indoles described in WO 95/08540, WO 99/00381 and U.S. Pat. No. 5,780,461 cited above are different compounds from those described in the present invention.

In the medical field, there is still a strongly perceived need for new therapeutic means which are useful for the treatment of tumours, to be used alone or in combination with other known antineoplastic drugs.

In this sector, there is also a strongly perceived need for new compounds endowed with antitumour and/or chemosensitising activity, i.e. compounds which are active against drug-resistant tumours and/or capable of making known antitumour drugs active against tumours against which they were ineffective owing to the onset of the above-mentioned conditions of drug resistance.

It has now been found that the formula (I) compounds are useful agents both as antitumour compounds and as chemosensitisers.

The chemosensitising mechanism of the compounds according to the invention described herein, i.e. their ability to bring about an inversion of drug resistance, is still unknown. It is thought to be related to mechanisms of interaction with the tumour cells and not with the antitumour drug to which the tumour cells have become resistant.

The experimental results obtained (reported here below) show that the formula (a) compounds, both alone and in combination with other known antiblastic drugs, are useful agents for the treatment of tumours.

Compounds with general formula (I) are therefore the object of the invention described herein.

A further object of the invention described herein are compounds with general formula (I) and their use in the medical field.

A further object of the invention described herein is a pharmaceutical composition containing as active ingredient a formula (I) compound and at least a pharmaceutically acceptable excipient and/or diluent.

A further object of the invention described herein are compounds with general formula (I) and a process for their preparation.

A further object of the invention described herein is a pharmaceutical composition containing as active ingredient a formula a) compound, for the treatment of a tumour pathology, in which the tumour is selected from the group consisting of sarcoma, carcinoma, carcinoid, bone tumour, neuroendocrine tumour, lymphoid leukaemia, acute promyelocytic leukaemia, myeloid leulaemia, monocytic leukaemia, megakaryoblastic leukaemia and Hodgkin's disease.

A further object of the invention described herein is a pharmaceutical composition containing as active ingredient a formula (I) compound, for the treatment of a tumour pathology, in which the tumour has shown drug resistance to the previous antibiotics used for its treatment, in which said formula (I) compound exerts a chemosensitising effect on said drug resistant tumour.

A further object of the invention described herein is a pharmaceutical composition containing as active ingredient a formula (I) compound, in combination with one or more known antitumour agents, in which the antitumour compound is selected from the group consisting of alkylating agents, topoisomerase inhibitors, antitubulin agents, intercalating compounds, anti-metabolites, natural products such as vinca alkaloids, epipodophyllotoxins, antibiotics, enzymes, taxans, and cytodifferentiating compounds.

Among the cytodifferentiating antitumour agents the one preferred is all-trans retinoic acid.

A further object of the invention described herein is the use of a formula (I) compound for the preparation of a medicine for the treatment of a tumour pathology.

A further object of the invention described herein is the use of a formula (I) compound for the preparation of a medicine for the treatment of a tumour pathology in which the tumour has shown drug resistance to the previous antitumour drugs used for its treatment, in which said formula (I) compound exerts a chemosensitising effect on said drug-resistant tumour.

A further object of the invention described herein is the use of a formula (I) compound, in combination with one or more known antitumour agents, for the preparation of a medicine for the treatment of tumour pathologies.

A further object of the invention described herein is the use of a formula (a) compound in combination with all-trans retinoic acid for the preparation of a medicine for the treatment of acute promyelocytic leukaemia.

The following examples further illustrate the invention.

EXAMPLE 1

The compound in example 1 was prepared using synthesis diagram 1 here below, in which steps A and B were conducted according to the procedures described by Casiraghi G. et al. Tetrahedron 1992, 48 (27), 5619; Casiraghi G. et al. J. Org. Chem 1994, 59 (7), 1801; Cornia M. et al. J. Org. Chem 1991, 56 (7), 5466; Cornia M. et al. Tetrahedron: Asymmetry 1997, 8 (17), 2905.

Scheme 1

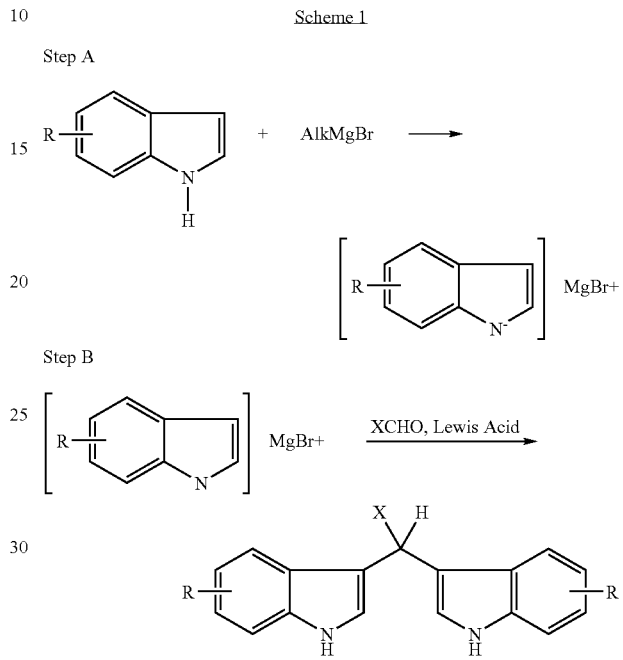

Step A
Preparation of Alkyl Magnesium Salts

To an anhydrous ether solution, containing 2 moles of alkyl-MgBr, prepared from 2 moles of alkyl-Br and 2 moles of Mg in anhydrous solvent (e.g. ethyl ether or tetrahydrofuran), were added 2 moles of indole, or of an indole derivative or one of its analogues, under stirring at ambient temperature.

The solvent was removed under vacuum and the residue was used directly in the next step.

Step B
Preparation of Bis-Indole Derivatives

The residue obtained from the previous step was dissolved in an inert organic solvent such as $CH_2Cl_2$ or $CHC_3$, or $CHCl_2CHCl_2$. Two or more moles of a Lewis acid were then added (e.g. $SnCl_4$, $TiCl_4$, $CeCl_3$, $TiCl(OPr)_3$) and 1 mole of aldehyde. The reaction was held under stirring for 12–72 hours at a temperature ranging from −80° C. to +80° C. At the end of this period the reaction was blocked with weakly alkaline neutral $H_2O$ with $NaHCO_3$, $Na_2CO_3$.

The organic phase was collected, washed with a small amount of $H_2O$, dried on anhydrous $MgSO_4$, filtered and concentrated to dryness. The end product was isolated and purified by means of the usual chromatographic systems.

EXAMPLE 1/1

Preparation of 2,3-5,6-di-O-isopropylidene-1,1-di-7-azaindol-3-yl-1-deoxy-D-mannitol (ST 1353)

To a solution in anhydrous $CH_2Cl_2$ (50 ml) of 7-azaindolyl-magnesium bromide 890 mg (4 mmol), prepared separately from 7-azaindole and ethyl-magnesium bromide in anhydrous ethyl ether, were added 4 ml of $SnCl_4$ in 1 M solution in anhydrous $CH_2Cl_2$ and 260.3 mg (1 mmol) of 2,3-5,6-di-O-isopropylidene-di-alpha-D-mannofuranose.

The reaction mixture was heated under reflux in a nitrogen atmosphere for 24 hours and then blocked by the addition of 50 ml of saturated aqueous solution of $NaHCO_3$. The resulting mixture was extracted with ethyl ether (3×100 ml) and the pooled extracts were washed with a small amount of $H_2O$, dried on $MgSO_4$, filtered and concentrated to dryness.

The crude residue was subjected to chromatography on an $SiO_2$ column using a hexane:ethyl acetate gradient ranging from 9:1 to 6:4 as the eluent. The pure product was isolated with a yield of 8%.

$C_{26}H_{30}N_4O_5$(478); melting point=decomposes at 210° C.; Rf=0.17 ($CH_2Cl_2/CH_3COCH_3$=1:1). $^1H$ ($CD_3OD$) δ=8.15–8.08 (2H, dd, CH aromatic); 8.10–8.05 (1H, d, CH aromatic); 7.95–7.9 (1H, d, CH aromatic); 7.60 (1H, s, CH aromatic); 7.08 (1H, s, CH aromatic); 7.06–6.95 (2H, m, CH aromatic); 5.05–5.35 (2H, 2m, CH aliphatic); 4.42 (1H, d, CH gem); 3.98–3.9 (1H, m, CH aliphatic); 3.84–3.76 (1H, m, CH aliphatic); 3.45–3.38 (1H, m, CH aliphatic); 1.45; 1.35; 1.16; 0.78 (12H, 4s, $CH_3$). MS (IS) M−=477. UA calculated C, 65.26; H, 6.32; N, 11.70. found C, 65.47H, 6.35 N, 12.01.

EXAMPLE 1/2

Preparation of 4,4-di-(7-azaindol-3-yl)-1-butanol (ST 1866)

This compound is prepared in the same way as described in example 1/1 starting from 7-azaindol and 2-methoxy-tetrahydrofuran.

$C_{18}H_{18}N_4O$ (306.37); melting point=decomposes at 221° C.; Rf=0.18 (hexane/AcOEt); $^1H$ ($CD_3OD$) δ=8.10 (2H, t, CH); 7.80 (7.8 d, 2H, d, CH); 7.30 (2H, s, $CH_2$); 6.90 (2H, m, CH); 4.40 (4.4 t, 1H, t, CH); 3.60 (t, 2H, t, $CH_2$); 2.30 (2H, m, $CH_2$); 1.60 (2H, m, $CH_2$). MS (IS) M−=305. ELEMENTAL ANALYSIS calculated C, 70.57; H, 5.92; N, 18.29. found C, 70.67; H, 5.6.00; N, 18.10.

EXAMPLE 2

The compounds in example 2 were prepared using synthesis in Scheme 2 here below.

Preparation of Bis-Indole Derivatives

In a solution of alcohol and water (for example, water and ethanol or methanol or isopropanol in various proportions) were dissolved 2 moles of indole and from 1 to 8 moles of butyraldehyde. The catalyst was then added in the form of an inorganic mineral acid (e.g. HCl), an organic acid (e.g. $CH_3COOH$), a Lewis acid (particularly effective are the lanthanide triflates, $Ln(OTf)_3$, that can also be recovered and reused).

The solution was held under stirring for 12–72 hours at a temperature ranging from 20° to 80° C. At the end of this period the alcohol was extracted with an organic solvent. The organic phase was washed with a small amount of $H_2O$ or alkaline $H_2O$, dried on anhydrous $Na_2SO_4$, filtered and concentrated to dryness.

The end product was isolated and purified by means of the usual chromatographic methods.

EXAMPLE 2/1

Preparation of 1,1-di-indol-3-yl-butane (ST 1385)

282 mg of indole (2.4 mmol) were dissolved in 10 ml of $CH_3OH$ and 5 ml of $H_2O$; 72 mg (1 mmol) of butyraldehyde and 240 mg of dysprosium triflate-$(CF_3SO_3)_3Dy$-(0.393 mmol) were added.

The resulting solution was stirred at ambient temperature for 24 hours. At the end of this period the methanol was removed under vacuum and the residue was extracted with ethyl acetate (3×50 ml). The organic extracts were pooled, washed with a small amount of water, dried on anhydrous $Na_2SO_4$, filtered and concentrated to dryness. The end product was isolated and purified on an $SiO_2$ column using a hexane:ethyl ether gradient ranging from 9:1 to 7:3 as the eluent.

284 mg of product were obtained with a yield of 84%.

$C_{20}H_{20}N_2$(288); melting point=150–151° C.; Rf=0.3 (ethyl ether/hexane 1:1); $^1H$ ($CD_3CN$) δ=9.10 (2H, br-s, NH); 7.60–7.50 (4H, d, H4'–H7'); 7.30 (2H, br-s, NH); 7.00–7.20 (4H, t, CH aromatic); 4.60 (1H, t, CH); 2.30 (2H,

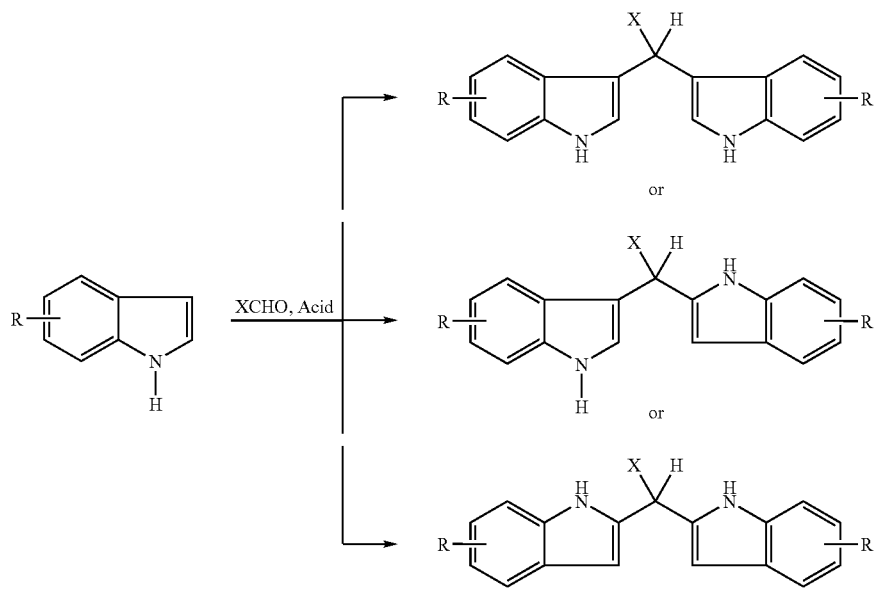

m, CH$_2$); 1.50 (2H, m, CH$_2$); 1.10 (3H, t, CH$_3$). MS (IS) M$^-$=287. ELEMENTAL ANALYSIS calculated (0.77% H$_2$O), C, 82.65; H, 7.02; N, 9.63. found C, 82.36; H, 7.17; N, 9.35.

EXAMPLE 2/2

Preparation of 1,1-di-(5 nitroindol-3-yl)-butane (ST 1429)

ST 1429 was prepared from 5-nitroindole and butyraldehyde prepared using the method described in example 2/1. The reaction, however, was heated under reflux for 48 hours.

The end product was purified by chromatography on SiO$_2$ using a hexane:ethyl ether gradient ranging from 6:4 to 2:8 as the eluent. Yield 85%.

C$_{20}$H$_{18}$N$_4$O$_4$ (378); Rf=0.4 (Et$_2$O/hexane=8:2); $^1$H (CDCl$_3$) δ=10.63 (2H, br, NH); 8.0 (2H, s, CH aromatic); 7.58 (2H, d, CH aromatic); 7.18–6.86 (4H, m, CH aromatic); 4.17 (1H, t, CH); 1.94–1.72 (2H, q, CH); 1.02–0.8 (2H, m, CH$_2$); 0.55 (3H, t, CH$_3$). MS (IS) M$^-$=377 ELEMENTAL ANALYSIS calculated C, 63.48; H, 4.79; N, 14.80. found C, 63.90; H, 4.75; N, 14.34.

EXAMPLE 2/3

Preparation of 1,1-di-(5-fluoroindol-3-yl)-butane (ST 1438)

This was prepared in the same way as described in example 2/2 starting from 5-fluoroindole and butyraldehyde. The reaction, however, was heated under reflux for 24 hours. The end product was isolated and purified by chromatography on an SiO$_2$ column using a hexane:ethyl ether gradient ranging from 7:3 to 4:6 as the eluent. Yield 45%.

C$_{20}$H$_{18}$F$_2$N$_2$ (324); melting point=decomposes at >200° C.; Rf=0.36 (hexane/AcOEt=7:3); $^1$H (CDCl$_3$) δ=8.95 (2H, br, NH); 7.35–7.02 (6H, m, CH aromatic); 6.92–6.8 (2H, m, CH aromatic); 4.33 (1H, t, CH gem); 2.18 (2H, q, CH$_2$); 1.44–1.32 (2H, m, CH$_2$); 0.96 (3H, t, CH$_3$). MS (IS) M$^-$=323; ELEMENTAL ANALYSIS calculated C, 74.05; H, 5.59; N, 8.63 F11.71. found C, 73.78H, 6.01; N, 8.29; F11.98.

EXAMPLE 2/4

Preparation of 1,1-di-(5-hydroxy indol-3-yl)-butane (ST 1393)

This was prepared according to the same procedure described in example 2/2 starting from 5-hydroxy-indole and butyiric aldehyde. The end product was purified chromatographically on an SiO$_2$ column using an ethyl ether:hexane gradient of 7:3. Yield 65%.

C$_{20}$H$_{20}$N$_2$O$_2$(320); melting point=decomposes at >200° C.; Rf=0.3 (ethyl ether:hexane 2:8) $^1$H (DMSO) δ=8.40 (2H, s, NH); 7.10–7.00 (2H, d, CH aromatic); 6.98–6.90 (2H, m, CH aromatic); 6.80–6.70 (2H, m CH aromatic); 6.60–6.40 (2H, m, CH aromatic); 4.20–4.00 (1H, t, CH); 2.10–2.0 (2H, m, CH$_2$); 1.40–1.20 (2H, m, CH$_2$); 1.00–0.80 (3H, t, CH$_3$). MS (IS) M$^-$=319; ELEMENTAL ANALYSIS calculated C, 74.97; H, 6.29; N, 8.74. found C, 74.57; H, 6.00; N, 8.41.

EXAMPLE 2/5

Preparation of 1,1-di-(5,6-methylenedioxy-indol-3-yl)-butane (ST 1478)

ST 1478 was prepared, as described in example 2/2, from 5,6-methylenedioxy-indole and butyraldehyde. The end product was isolated and purified by chromatography on an SiO$_2$ column using a hexane:ethyl acetate gradient of 7:3 as the eluent. Yield 38%.

C$_{22}$H$_{20}$N$_2$O$_4$ (376); melting point=decomposes at >200° C.; Rf=0.58 (hexane/AcOEt 6=4); $^1$H (CD$_3$CN): δ=9.10–8.90 (2H, br-s, NH); 7.20 (1H, s, CH aromatic); 7.00 (2H, d, CH aromatic); 6.80–6.90 (2H, d, CH aromatic); 6.30 (1H, s, CH); 5.90 (4H, s, CH$_2$); 4.30 (1H, t, CH); 2.30 (2H, m, CH$_2$); 1.50 (2H, m, CH$_3$); 1.10 (3H, t, H4). MS (IS) M$^-$=375. ELEMENTAL ANALYSIS calculated C 66.65; H, 6.10; N, 7.06. found C, 65.98H, 5.90; N, 6.96.

EXAMPLE 2/6

Preparation of 1,1-di-(indol-3-yl)-cyclohexylmethane (ST 1487)

ST 1487 was prepared as described in example 2/2 from indole and cyclohexanecarboxyaldehyde.

The reaction, however, was heated under reflux for 48 hours.

The end product was purified chromatographically on an SiO$_2$ column using hexane/ether 7:3 as the eluent. Yield 75%.

C$_{23}$H$_{24}$N$_2$ (328); melting point=decomposes at >210° C.; Rf=0.20 (hexane/Et$_2$O=6:4); $^1$H (CDCl$_3$) δ=7.84 (2H, br, NH); 7.63 (2H, d, CH aromatic); 7.25 (2H, d, CH aromatic); 7.18–6.90 (4H, m, CH aromatic); 4.25 (1H, d, CH); 2.35–2.15 (1H, m, CH); 1.90–0.85 (10H, mm, CH$_2$). MS (IS) M$^-$=327;

ELEMENTAL ANALYSIS calculated C, 84.10; H, 7.36; N, 8.52. found C, 83.81; H, 7.43; N, 8.30.

EXAMPLE 2/7

Preparation of 1,1-di-(7-azaindol-3-yl)-butane (ST 1436)

ST 1436 was prepared as described in example 2/2 from 7-azaindole and butyraldehyde. The reaction, however, was heated under reflux for 48 hours. The end product was isolated and purified chromatographically on a silica column eluting with a CH$_2$Cl$_2$:CH$_3$COCH$_3$ gradient ranging from 9:1 to 4:6. Yield 15%.

C$_{18}$H$_{18}$N$_4$(291); melting point=decomposes at >200° C. Rf=0.26 (CH$_2$Cl$_2$/CH$_3$COCH$_3$=6:4); $^1$H (DMSO-D$_6$) δ=11.32 (2H, br, NH); 8.12 (2H, d, CH aromatic); 7.85 (2H, d, CH aromatic); 7.40 (2H, s, CH aromatic); 6.98–6.82 (2H, m, CH aromatic); 4.35 (1H, t, CH); 2.15 (2H, q, CH$_2$); 1.35–1.05 (2H, m, CH$_2$); 0.88 (3H, t, CH3 aliphatic). MS (IS) M$^-$=290; ELEMENTAL ANALYSIS calculated C, 74.95; H, 6.24; N, 19.29. found C, 74.52H, 6.38; N, 18.98

EXAMPLE 2/8

Preparation of 1,3-dihydroxy-2,2-(diindol-3-yl)-propane (ST 1368)

The compound was prepared as described in example 2/4 substituting dihydroxyacetone for aldehyde. Yield 60%.

C$_{19}$H$_{18}$N$_2$O$_2$(306.3); melting point=decomposes at 223° C.; (α)$_D$=23.8° (0.4% CHCl$_3$); Rf=0.77 (ethyl ether); $^1$H (CD$_3$OD) δ=7.30–7.20 (4H, m, CH aromatic); 7.70–7.60 (2H, m, CH aromatic); 7.30–7.05 (4H, m, CH aromatic); 7.04–6.96 (2H, d, CH aromatic); 6.90–6.80 (2H, m, CH); 6.62–6.58 (2H, m, CH aromatic); 4.40 (4H, s, CH$_2$). MS (IS) M- (—H$_2$O)=287; Elemental analysis: calculated C, 74.48; H, 5.92; N, 9.14. found C, 74.08; H, 5.65; N, 8.97.

EXAMPLE 2/9

Preparation of 1,1-diindol-3-yl-tetradecane (ST 1369)

The compound was prepared as described in example 2/4, reacting the indole with tetradecane aldehyde. Yield 80%.

$C_{30}H_{40}N_2$(428.6); melting point=softens at 50° C.; Rf=0.28 (hexane/AcOEt 85:15); $^1$H (CDCl$_3$) δ=7.80 (2H, s, NH); 7.60–7.44 (2H, d, CH aromatic); 7.30–7.20 (2H, d, CH aromatic); 7.10–7.00 (2H, m, CH aromatic); 7.00–6.90 (4H, m, CH aromatic); 4.42–3.938 (1H, t, CH), 2.20–2.00 (2H, m, CH$_2$); 1.40–1.00 (22H, m, CH$_2$); 0.90–0.70 (3H, t, CH$_3$). MS (IS) M$^+$ (+Na)=451. ELEMENTAL ANALYSIS calculated C, 84.05; H, 9.40; N, 6.53. found C, 83.70; H, 9.77; N, 6.17.

EXAMPLE 2/10

Preparation of 1,1-di-indol-3-yl-1-deoxy-D-glucose (ST 1350)

The compound was prepared as described in example 2/4 recating indole with glucose. Yield 60%.

$C_{22}H_{24}N_2O_5$(396.45); melting point=decomposes at 60° C.; $(α)_{Dc}$=+66.30 (0.5% CH$_3$OH); Rf=0. (CHCl$_3$/CH$_3$OH 7:3); $^1$H (CD$_3$OD) δ=7.70 (1H, d, CH aromatic); 7.60 (1H, d, CH aromatic); 7.40 (1H, s, CH aromatic); 7.30–7.20 (2H, m, CH aromatic); 7.10 (1H, s, CH aromatic); 7.10–6.8 (4H, m, CH aromatic); 5.0 (1H, d, CH); 4.70–4.60 (1H, dd, CH); 3.92–3.85 (1H, m, CH); 3.80–3.60 (3H, m, CH$_2$ OH and CH); 3.58–3.40 (1H, m, CH). MS (IS) M$^-$=395. Elemental analysis: calculated (2.2% H$_2$O) C, 65.18; H, 6.20; N, 6.87. found C, 65.10; H, 6.23; N, 6.40.

EXAMPLE 2/11

Preparation of (R,S)-1,1-(indol-2-yl, indol-3-yl) butane (ST 1625)

282 mg of indole (2.4 mmol) were dissolved in 10 ml of CH$_3$OH and 5 ml of HCl 1N. 72 mg (1 mmol) of butyraldehyde were added.

The resulting solution was heated at a temperature of 80° C. for 16 hours. At the end of this period the methanol was removed under vacuum and the residue was extracted with CH$_2$Cl$_2$. The organic extracts were pooled, washed with water, dried on anhydrous Na$_2$SO$_4$, filtered and concentrated to dryness. The end product was isolated and purified chromatographically on an SiO$_2$ column using a hexane:ethyl ether gradient ranging from 9:1 to 7:3 as the eluent. Yield 62%.

$C_{20}H_{20}N_2$(288) melting point=decomposes at >250° C.; Rf=0.25 (ethyl ether/hexane 1:1); $^1$H (CDCl$_3$) δ=8.10 (1H, br-s, NH); δ=7.80 (1H, br-s, NH); 7.60–7.50 (4H, d, CH aromatic); 7.30 (1H, br-s, NH); 7.20–7.00 (4H, t, CH aromatic); 6.50 (1H, br-s, CH); 4.60 (1H, t, CH); 2.30 (2H, m, CH$_2$); 1.50 (2H, m, CH$_2$); 1.10 (3H, t, CH$_3$). MS (IS) M$^-$=287. Elemental analysis: calculated C, 83.29; H, 6.99; N, 9.71. found C, 82.77; H, 6.90; N, 9.41.

EXAMPLE 2/12

Preparation of (R,S)-5-hydroxy-1,1-(indol-2-yl, indol-3-yl)-pentane (ST 1345)

This was prepared as described in example 2/11 reacting indole with 5-hydroxypentanal. Yield 40%.

$C_{21}H_{22}N_2O$ (31.42); melting point=decomposes at 200° C.; Rf=0.5 (hexane/is PrOH 97.5:2.5); $^1$H (CDCl$_3$) δ= 8.00 (1H, s, NH); 7.8 (1H, s, NH); 7.54–7.48 (1H, m, CH aromatic); 7.40–7.36 (1H, d, CH aromatic); 7.30–7.20 (1H, d, CH aromatic); 7.1–6.86 (6H, m, CH aromatic); 6.40 (1H, s, CH aromatic); 4.30 (1H, t, CH); 3.5 (2H, t, CH$_2$); 2.20–2.00 (2H, m, CH$_2$); 1.60–1.40 (2H, m, CH$_2$); 1.40–1.20 (3H, m, CH$_2$ e OH). MS (IS) M$^-$=317. Elemental analysis: calculated C, 79.21; H, 6.96; N, 8.79. found C, 78.64; H, 7.15; N, 8.45.

EXAMPLE 2/13

Preparation of R,S-5-hydroxy-1,1-(5,6-methylenedioxy-indol-2-yl, 5,6 methylenedioxy-indol-3-yl) pentane (ST 1423)

This was prepared as described in example 2/11 starting from the 5,6-methylenedioxy derivative of indolo. Yield 20%.

$C_{23}H_{22}N_2O_5$(406); melting point=decomposes at 220° C.; Rf=0.63 (hexane/iPrOH=97.5/2.5); $^1$H (CD3CN) δ=9.1–8.90 (2H, br-s, NH); 7.20 (1H, s, CH aromatic); 7.00 (2H, d, CH aromatic); 6.80–6.90 (2H, d, CH aromatic); 6.30 (1H, s, CH aromatic); 5.90 (4H, s, CH$_2$); 4.30 (1H, t, H1); 3.50 (2H, m, H5); 2.20 (2H, m, CH$_2$); 1.40–1.60 (2H, m, CH$_2$). MS (IS) M$^+$=407. Elemental analysis: calculated C, 67.98; H, 5.42; N, 6.89. found C, 67.90; H, 5.50; N, 6.82;

EXAMPLE 2/14

Preparation of [di-(2-pyrryl)-phenyl]-methane (ST 1430)

This was prepared as described in example 2/4, reacting the pyrrole derivative with benzaldehyde. Yield 40%.

$C_{15}H_{14}N_2$(222) Rf=0.25 (hexane/AcOEt=8:2); melting point=decomposes at 200° C.; $^1$H (CDCl$_3$) δ=7.90 (2H, br-s, NH); 7.30 (5H, m, CH aromatic); 6.70 (2H, m CH aromatic); 6.20 (2H, s CH aromatic); 5.90 (2H, s, CH aromatic); 5.50 (1H, s, CH). MS (IS) M$^-$=221. Elemental analysis: calculated C, 67.56; H, 6.30; N, 12.61. found C, 67.90; H, 6.50; N, 12.45.

EXAMPLE 2/15

Preparation of di-(5-ethoxycarbonyl-pyrrol-2-yl)-phenyl-methane (ST 1431)

This was prepared as described in example 2/14 reacting the pyrrole derivative with benzaldehyde. Yield 30%.

$C_{21}H_{22}N_2O_4$(366); melting point=decomposes at 200° C.; Rf=0.25 (hexane/AcOEt=7:3); $^1$H(CDCl$_3$) δ=9.40 (2H, br-s, NH); 7.30 (5H, m, CH aromatic); 5.90–6.80 (4H, t, CH aromatic); 5.50 (1H, s, CH); 4.20 (4H, q, CH$_2$); 1.30 (6H, t, CH3). MS (IS) M$^-$=365. Elemental analysis: calculated C, 57.37; H, 6.01; N, 7.65. found C, 57.00; H, 6.50; N, 7.52.

EXAMPLE 2/16

Preparation of 1,1-di-(2-pyrryl)-butane (ST 1432)

This was prepared as described in example 2/4, reacting the pyrrole derivative with butyraldehyde. Yield 45%.

$C_{12}H_{16}N_2$(188); melting point=decomposes at 200° C.; Rf=0.32 (hexane/AcOEt/NEt$_3$=80:19:1); $^1$H (CDCl3): 7.40 (2H, br-s, NH); 6.60 (2H, s, CH aromatic); 6.20 (2H, s, CH aromatic); 6.10 (2H, s, CH aromatic); 4.00 (1H, t, CH); 2.00 (4H, q, CH$_2$); 1.30 (3H, m, CH$_3$). MS (IS) M$^-$=187. Elemental analysis: calculated C, 76.59; H, 8.51; N, 14.89. found C, 76.44; H, 8.50; N, 14.38.

EXAMPLE 2/17

Preparation of 4,4-di-(1H-indolyl-)butanoic acid (ST 1961)

282 mg of indole (2.4 mmol) were dissolved in 10 ml of $CH_3OH$ and 5 ml of $H_2O$; 102 mg of semisuccinic aldehyde (1 mmol) and 240 mg of dysprosium triflate-$(CF_3SO_3)_3Dy$-(0.393 mmol) were added. The resulting solution was stirred at 35° C. for 24 hours. At the end of that period the methanol was removed under vacuum and the residue was extracted with ethyl acetate (3×50 ml). The organic extracts were pooled, washed with a small amount of water, dried on anhydrous $Na_2SO_4$, filtered and concentrated to dryness. The end product was isolated and purified chromatographically on an $SiO_2$ column, using a hexane:isopropyl alcohol gradient ranging from 9:1 to 8:2.

108 mg of product were obtained with a yield of 34%.

$C_{20}H_{18}N_2O_2$ (318.37); melting point=decomposes at >200° C.; Rf=0.31 (hexane/isopropyl alcohol 8:2); $^1H$ (DMSO-D6) δ=9.18 (2H, br-s, NH); 7.55 (2H, d, CH aromatic); 7.30 (2H, t, CH aromatic); 7.14–6.82 (6H, m, CH aromatic); 5.40(1H, br-s, COOH); 4.45(1H, t, CH); 2.58–2.39 (2H, m, $CH_2$); 2.39–2.25 (2H, m, $CH_2$). MS (IS) M⁻=317. Elemental analysis: calculated C 75.45; H 5.70; N 8.80. found C 75.12; H 5.49; N 8.56.

EXAMPLE 2/18

Preparation of 4-hydroxy-1,1-di-(5,6-methylenedioxy-indol-3-yl)-butane (ST1730)

The compound was prepared as in example 2/4 starting from 5,6-methylenedioxy-indole and 2-methoxy-tetrahydrofuran. Yield 35%.

$C_{22}H_{20}N_2O_5$ (392.41); melting point=decomposes at >240° C.; Rf=0.44 (hexane/iPrOH=75/25); $^1H$ ($CD_3CN$) δ=9.00 (2H, broad, NH); 7.20 (2H, s, CH aromatic); 6.90 (4H, m, CH aromatic); 6.00 (4H, m, $CH_2$); 4.30 (1H, t, CH); 3.60 (2H, q, $CH_2$); 2.30 (2H, m, $CH_2$); 1.60 (2H, m, $CH_2$). MS (IS) M⁺=393. Elemental analysis: calculated C, 67.34; H, 5.14; N, 7.14. found C, 67.30; H, 5.20; N, 7.100.

EXAMPLE 2/19

Preparation of (R,S)-4-hydroxy-1,1-di-(5,6-methylenedioxy-indol-2-yl, 5,6-methylenedioxy-indol-3-Yl)-butane (ST 1731).

The compound was prepared as described in example 2/11 starting from the 5,6-methylenedioxy-indole of the indole. Yield 15%.

$C_{22}H_{20}N_2O_5$ (392.41); melting point=decomposes at 205° C.; Rf=0.41 (hexane/iPrOH=75/25); $^1H$ ($CD_3CN$) δ=9.10 (1H, broad, NH); 8.90 (1H, broad, NH); 7.20 (1H, s, CH aromatic); 7.00 (2H, s, CH aromatic); 6.90–6.80 (2H, m, CH_aromatic); 6.40 (1H, s, CH aromatic); 6.00 (4H, m, $CH_2$); 4.30 (1H, t, CH); 3.70 (2H, m, $CH_2$); 2.20 (2H, m, $CH_2$); 1.60 (2H, m, $CH_2$). MS (IS) M⁻=391. Elemental analysis: calculated C, 67.34; H, 5.14; N, 7.14. found C, 67.14; H, 5.36; N, 7.10

EXAMPLE 2/20

Preparation of 1,1-di(indol-3-yl)-4-hydroxy-butane (ST 1707).

The compound was prepared in the same way as described in example 2/4, starting from indole and 2-methoxy-tetrahydrofuran.

$C_{20}H_{20}N_2O$ (304.39); melting point=110–115° C.; Rf=0.26 (hexane/AcOEt=1/1); $^1H$ ($CD_3CN$) δ=10.70 (2H, broad, NH); 7.50 (2H, d, CH aromatic); 7.20 (4H, m, CH aromatic); 6.90 (2H, m, CH aromatic); 6.80 (2H, m, CH aromatic); 4.30 (1H, t, CH); 3.40 (2H, m, $CH_2$); 2.20 (2H, m, $CH_2$); 1.40 (2H, m, $CH_2$). MS (IS) M⁻=303. Elemental analysis: calculated C, 78.92; H, 6.62; N, 9.20. found C, 78.88; H, 6.70; N, 9.10.

EXAMPLE 2/21

Preparation of 4-hydroxy-1,1-di-(5,6-methylenedioxy-indol-3-yl)-butane (ST 1750).

The compound was isolated in the reaction mixture of example 2/20.

$C_{22}H_{20}N_2O_5$ (392.41); melting point=decomposes at 250° C.; Rf=0.60 (hexane/iPrOH=75/25; $^1H$ ($CD_3CN$) δ=9.10 (2H, broad, NH); 7.00–6.90 (4H, m, CH aromatic); 6.40 (2H, s, CH aromatic); 6.00 (4H, s, $CH_2$); 4.30 (1H t, CH); 3.60 (2H q, $CH_2$); 2.30 (2H, m, $CH_2$); 1.60 (2H, m, $CH_2$). MS (IS) M⁻=391. Elemental analysis: calculated C, 67.34; H, 5.14; N, 7.14. found C, 67.26; H, 5.35; N, 7.10.

EXAMPLE 2/22

Preparation of 1,1-di-(5-hydroxy-indol-3-yl)-5-hydroxy-pentane

The compound was prepared as in example 2/4, starting from 5 hydroxy-indole.

$C_{21}H_{22}N_2O_3$ (350.42); melting point=decomposes at >200° C.; Rf=0.58 (AcOEt); $^1H$ ($CD_3OD$) δ=7.20–7.00 (2H, d, CH aromatic); 7.00–6.90 (2H, m, CH aromatic); 6.90–680 (2H, m, CH aromatic); 6.70–6.50 (2H, m, CH aromatic); 4.30–4.20 (1H, t, CH); 3.60–3.40 (2H, t, $CH_2$); 2.30–2.05 (2H, m, $CH_2$); 1.70–1.50 (2H, m, $CH_2$); 1.50–1.40 (2H, m, $CH_2$). MS (IS) M⁻=349. Elemental analysis: calculated C, 71.97; H, 6.32, 7.99. found C, 71.00; H, 6.46; N, 7.50.

EXAMPLE 3

The compound in example 3 was prepared using synthesis in Scheme 3 here below, in which step A is conducted according to the procedures described by Dondoni G. et al. Tetrahedron Lett. 1992, 33 (29), 4221; Dondoni G. et al. Synth. Commun. 1994, 24 (18), 2537.

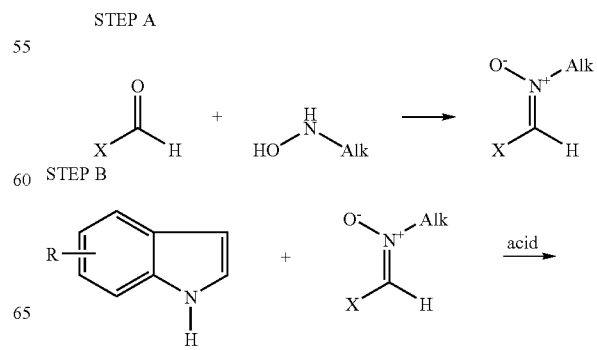

Scheme 3

-continued

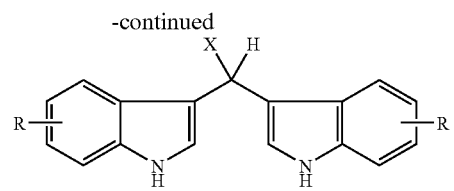

Step A
Preparation of the Nitrone Derivative
Step B
Preparation of the Bis-Indole Derivative The nitrone derivative from step A was dissolved in an anhydrous solvent (e.g. CH$_2$Cl$_2$, AcOEt, THF, dioxane) together with indole in stoichiometric amounts or in excess. To the solution thus obtained an organic or inorganic acid (e.g. HCl, acetic acid, trifluoroacetic acid, SnCl$_4$, trimethylsilyl chloride) was added at room temperature. The reaction was processed on disappearance of the indole or indole derivative, adding organic solvent and shaking it vigorously with a basic aqueous solution to eliminate the acidity of the solution. The organic solution, after drying with a dehydrating agent, was concentrated. The solid residue was subjected to chromatography on silica gel to isolate and purify the bis-indole derivative.

EXAMPLE 3/1

Preparation of (2S)-2,3-O-isopropylidene-2,3-dihydroxy-1,1-diindol-3-yl-propane (ST 1330)

2,3-O-isopropylidene-glyceraldehyde (1.8 g, 14 mmol) (prepared fresh from the diisopropylidene derivative of D-mannitol) and N-benzyl-hydroxylamine (1.23 g, 10 mmol) were dissolved in 20 ml of CH$_2$Cl$_2$ in a flask. 10 g of Na$_2$SO$_4$ were suspended in the solution and left to stir for 16 hours at ambient temperature. At the end of the reaction, the solution was filtered and concentrated until a solid was obtained which was then crystallised with hexane. The nitrone derivative was obtained as a white solid (2.1 g, yield 89%).

Part of this solid (1.2 g, 5.11 mmol), placed in a flask, was dissolved in anhydrous CH$_2$Cl$_2$ (30 ml) with indole (1.5 g, 12.8 mmol) and 20 ml of CH$_2$Cl$_2$ were added drop-wise to the resulting solution at ambient temperature.

After 16 hours of stirring at ambient temperature, the reaction mixture was processed by dissolving it with CH$_2$Cl$_2$ (70 ml) and shaking it vigorously with a saturated solution of NaHCO$_3$. After separation in a funnel, the organic phase was concentrated to dryness. The solid obtained was submitted to chromatography on silica gel (ethyl ether:hexane 1:1) yielding (2S)-2,3-O-isopropylidene-2,3-dihydroxy-1,1-diindol-3-yl-propane (1.59 g, yield 90%).

C$_{22}$H$_{22}$N$_2$O$_2$(346.4); melting point=decomposes at 100–110° C.; ($\alpha$)$_D$=18.3° (0.5% CHCl$_3$); Rf=0.5 (ethyl ether:hexane 1:1); $^1$H (CDCl$_3$) $\delta$=8.00 (2H, s, NH); 7.60–7.44 (2H, dd, CH aromatic); 7.26–7.24 (2H, dd, CH aromatic); 7.20–6.86 (6H, m, CH aromatic); 5.00–4.84 (1H, m CH); 4.64 (1H, d, CH); 4.00–3.80 (2H, dd, CH); 1.40 (6H, s, CH$_3$). MS (IS) M$^-$=345. Elemental analysis: calculated (4% H$_2$O, 2.3% AcOEt) C, 74.34; H, 6.50; N, 7.70. found C, 74.66; H, 6.84; N, 7.26.

EXAMPLE 4

The compounds in example 4 were prepared using synthesis in Scheme 4 here below.

Scheme 4

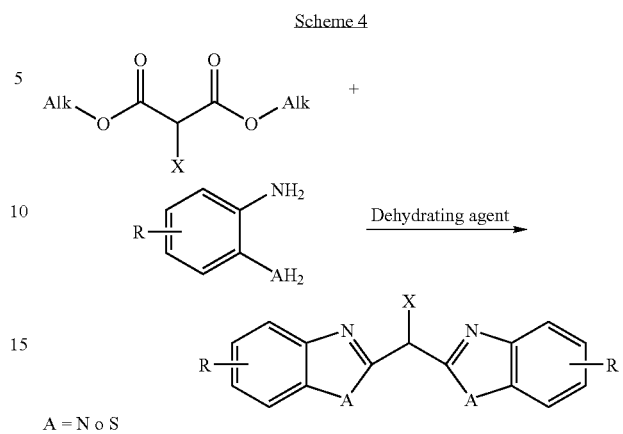

A = N o S

Preparation of bis-benziimidazole and bis-benzothiazole Derivatives:

In a flask equipped with good stirring were added a dehydrating agent (e.g. polyphosphoric acid or its esters, thionyl chloride, phosphoric anhydride) (1.5 up to 20 mol), malonic ester derivatives (1–2 mol) and 1,2-phenyldiamine or its derivatives (1–4 mol) to obtain the bis-benziimidazoles, or 2-thioaminophenyl or its derivaties (1–4 mol) to obtain the bis-benzothiazoles. On completing all the additions, the mixture was heated very slowly to 160–200° C. and left at this temperature for another 20–30 hours, in an anhydrous milieu and a deoxygenated atmosphere. At the end of this period, a basic aqueous solution together with an organic solvent immiscible in water (e.g. methylene chloride, ethyl acetate, ethyl ether, tetrahydrofuran) was added to the cooled mixture. After complete dissolution, the organic phase was separated from the aqueous phase and concentrated, obtaining a semisolid crude reaction product.

All end products were isolated and purified from the crude reaction product by means of direct-phase chromatography on silica gel.

EXAMPLE 4/1

Preparation of phenyl-dibenzothiazol-2-yl-methane (ST 1433)

6 g of PPA (polyphosphoric acid), 2.54 ml of 2 aminothiophenol (technical 90%) (23 mmol) and 2.60 ml (11 mmol) of diethyl-phenylmalonate were added to a flask rendered anhydrous and in an argon atmosphere. This mixture was subjected to slow heating to 140–145° C. and then left at this temperature for approximately 16 hours or until the amine disappeared.

The reaction was processed by adding ethyl acetate (300 ml) and a saturated solution of bicarbonate of sodium (200 ml). The organic phase was separated from the aqueous phase and vacuum concentrated until all the solvent was completely eliminated. The resulting solid was subjected to purification on a silica gel chromatography column (mobile phase hexane:dioxane gradient up to 8:2) obtaining 500 mg of end product (yield 12%).

C$_{21}$H$_{14}$N$_2$S$_2$(358.5); melting point=178° C.; Rf=0.41 hexane/dioxane 8:2); $^1$H (DMSO) $\delta$=7.80–7.70 (3H, m, CH aromatic); 7.60–7.40 (5H, m, CH aromatic); 7.40–7.20 (3H, m, CH aromatic); 7.20–7.00 (3H, m, CH aromatic, CH). MS (IS) M$^+$ (—H$_2$O)=359. Elemental analysis: calculated C, 70.36; H, 3.93; N, 7.81. found C, 70.10; H, 3.85; N, 7.49.

EXAMPLE 4/2

Preparation of 1,1-di-(benzimidazol-2-yl)-butane (ST 1435)

3 g of PPA together with 1,165 g (11 mmol) of 1,2-phenyldiamine and 1,153 ml (5.5 mmol) of diethyl-propylmalonate were placed in an anhydrous milieu an argon atmosphere in a flask equipped with stirring. On completing the additions, the reaction mixture was heated slowly to 150–155° C. and held at that temperature for another 16 hours. At the end of this period, after cooling, a saturated solution of sodium bicarbonate (100 ml) and ethyl acetate (150 ml) was added to the reaction mixture. After purification of the crude product on a silica gel flash chromatography column (mobile phase hexane: THF 8:2) the desired product was obtained. Yield 10%.

$C_{18}H_{18}N_4$(290.3); melting point=decomposes at 260° C.; Rf=0.38 (AcOEt/MeOH 95:0.5); $^1H$ (DMSO+D2O) δ=7.50–7.40 (4H, m, CH aromatic); 7.20–7.00 (4H, m, CH aromatic); 4.60–4.50 (1H, t, CH); 2–40–2.20 (2H, m, CH2); 1.40–1.20 (2H, m, $CH_2$); 1.00–0.90 (3H, t, $CH_3$). MS (IS) $M^-$=289. Elemental analysis: calculated C, 74.45; H, 6.24; N, 19.29. found C, 74.21; H, 5.98; N, 18.90.

EXAMPLE 5

The compound in example 5 was prepared using synthesis in Scheme 5 here below:

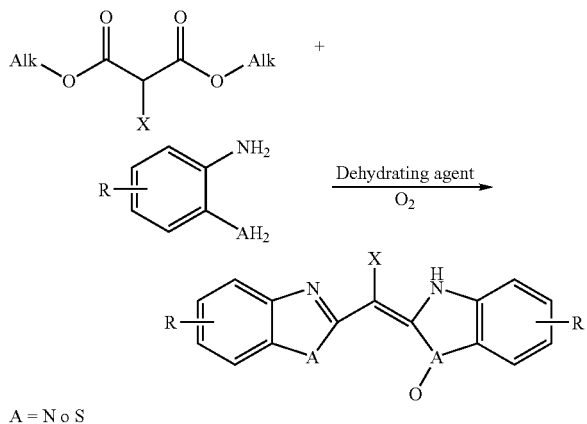

Scheme 5

A = N o S

Preparation of N-oxo bis-benziimidazole and S-oxo bis-benzothiazole Derivatives

To a flask equipped with good stirring were added a dehydrating agent (e.g. polyphosphoric acid or its esters, thionyl chloride, phosphoric anhydride) (1.5 up to 20 mol), malonic ester derivatives (1–2 mol) and 1,2-phenyldiamine or its derivatives (1–4 mol) to obtain the bis-benziimidazoles, or 2-thioaminophenyl or its derivatives (1–4 mol) to obtain the bis-benzothiazoles. On completing all these additions, the mixture was heated very slowly to 160–200° C. and left at this temperature for a further 20–30 hours.

At the end of this period, to the cooled mixture was added a basic aqueous solution together with an immiscible organic solvent (e.g. methylene chloride, ethyl acetate, ethyl ether, or tetrahydrofuran). After complete dissolution, the organic phase was separated from the aqueous phase and concentrated, obtaining a semisolid crude reaction product. All the end products were isolated and purified from the crude reaction product by direct-phase chromatography on silica gel.

EXAMPLE 5/1

Preparation of (benzothiazol-2-yl, benzothiazol-3 oxid-2-yl) phenyl-methane (ST 1424)

6 g of PPA (polyphosphoric acid), 2.54 ml of 2 aminothiophenol (technical 90%) (23 mmol) and 2.60 ml (11 mmol) of diethyl-phenylmalonate were placed in a flask equipped with good stirring. The reaction mixture was subjected to slow heating to 140–160° C. and was then left at this temperature for approximately 16 hours.

At the end of this period, the reaction was processed by adding ethyl acetate (300 ml) and shaking vigorously with a saturated sodium bicarbonate solution (200 ml). The organic phase was separated from the aqueous phase and vacuum concentrated. The resulting solid was subjected to a first purification on a silica gel chromatography column (hexane: dixoane 8:2) and then to a second purification on a reverse-phase preparatory HPLC column (Hibar column, 250×25 mm, RP-18; flow rate 10 ml/min; RT 28 min; UV detector 360 nm). Benzothiazol-2-yl, benzothiazol-3 oxid-2-yl)-phenyl-methane was obtained with a yield of 15%.

$C_{21}H_{14}N_2OS_2$(374.5); melting point=152° C.; Rf=0.33 (hexane/dioxane 8:2); $^1H$ (DMSO) δ=8.5 (1H, s, NH); 8.14–8.08 (2H, d, CH aromatic); 8.04–7.98 (2H, d, CH aromatic); 7.80–7.68 (2H, d, CH aromatic); 7.60–7.40 (7H, m, CH aromatic). MS (IS) $M^+$(—$H_2O$)=357. Elemental analysis: calculated C, 67.38; H, 3.70; N, 7.47. found C, 67.39; H, 3.80; N, 7.39.

EXAMPLE 6

The compound in example 6 was prepared using synthesis in Scheme 6 here below, in which step A is conducted according to the procedure described by Diez-Barra E. et al., Synth Commun. 1993, 23(13), 1783; and step B is conducted according to the procedure described by H. Lasta D. J. Tetrahedron Lett. 1990, 31 (41), 5833.

Scheme 6

Step A

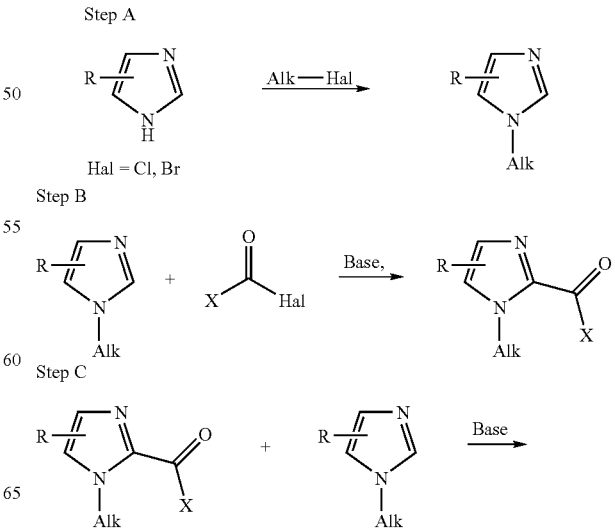

Hal = Cl, Br

Step B

Step C

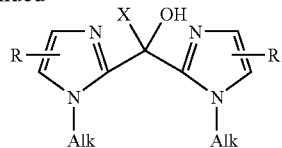

Step A
Preparation of N-alkyl Derivatives of imidazole
Step B
Preparation of N-alkyl-2-alkanoyl or N-alkyl-2-aroyl Derivatives of N-alkyl imidazole
Step C
Preparation of bis-imidazole Derivatives One mole of N-allyl imidazole (produced according to the procedure described by Diez-Barra E. et al., Synth Commun 1993, 23(13), 1783) was dissolved in an organic solvent rendered anhydrous (e.g. hexane, ethyl ether, dioxane, or terahydrofuran) in a flask equipped with stirring, in an anhydrous milieu and under an inert atmosphere. To this solution, at low temperature (from −10 to −70° C.) was added a solution or dispersion of basic reagent (e.g. butyl lithium, sodium hydride, lithium dialkylamine, sodium amide, t-butyl lithium) in molar amounts or in slight excess. At the end of the addition, after leaving the mixture to react for a further period (from 10 min to 1 hour), a solution of the ketone derivative of N-allyl imidazole (produced according to the procedure described by H. Lasta D. J. Tetrahedron Lett. 1990, 31 (41), 5833) was added dropwise in stoichiometric amounts or in excess in relation to the N-allyl imidazole (from 1 to 2 mmol).

After another 30 minutes at the initial temperature, the reaction mixture was left to warm up to ambient temperature (25–30° C.) and under stirring until the N-alkyl imidazole had completely disappeared. To the reaction mixture were added organic solvent and a saturated aqueous solution of sodium chloride. After separation of the organic solvent from the aqueous phase, the latter was dried on sodium sulphate and concentrated. The resulting solid was subjected to chromatography on silica gel or to crystallisation, obtaining the products desired.

EXAMPLE 6/1

Preparation of phenyl, hydroxy, di-(N,N-dibenzyl-imidazol-2-yl) methane (ST 1440)

A solution of 0.8 g (5 mmol) of N-benzyl imidazole (produced according to the procedure described by Diez-Barra E. et al., Synth Commun 1993, 23(13), 1783) in 10 ml of anhydrous THF was cooled to −70° C. On reaching this temperature, 3.5 ml (5.6 mmol) of a solution of n-butyl lithium 1.6 M in hexane (5.6 mmol) were added. Subsequently, 1.47 g (5.6 mmol) of N-benzyl-2-benzoyl imidazole (produced according to the procedure described by H. Lasta D. J. Tetrahedron Lett. 1990, 31 (41), 5833) previously dissolved in THF (1.5 ml) were added drop-wise. On completing the addition, the reaction mixture was brought up to the temperature of 25° C. and held under stirring for 16 hours. At the end of this period, the solution was diluted with 200 ml of CH$_2$Cl$_2$ and shaken vigorously with a saturated solution of NaCl (100 ml). The organic phase separated from the aqueous phase was dried with Na$_2$SO$_4$ and concentrated. A crude solid was obtained which was purified by crystallising it with ethyl acetate, obtaining phenyl, hydroxy, di-(N,N-dibenzyl-imidazol-2-yl) with a yield of 71.4%.

C$_{27}$H$_{24}$N$_4$O (420.51); melting point=decomposes at 160° C.; Rf=0.72 (AcOEt/NH$_3$ 98:0.2); $^1$H (CDCl$_3$) δ=7.30–7.10 (12H, m, CH aromatic, OH); 7.00 (2H, S, CH imid.) 6.98–6.82 (4H, m, CH aromatic); 6.80 (2H, s, CH imid.; 5.40 8 (4H, d, CH$_2$). MS (IS) M$^+$=421. Elemental analysis: calculated C, 77.11; H, 5.75; N, 13.32. found C, 77.07; H, 5.44; N, 13.45.

EXAMPLE 7

The compound in example 7 was prepared using synthesis in Scheme 7 here below, in which step A is conducted according to the procedure described by Cornia M. et al., Tetrahedron: asymmetry 1997, 8 (17) 2905; Casiraghi G. et al., Tetrahedron 1992, 48 (27), 5619, and the procedure described in example 1 step A.

Scheme 7

Step A

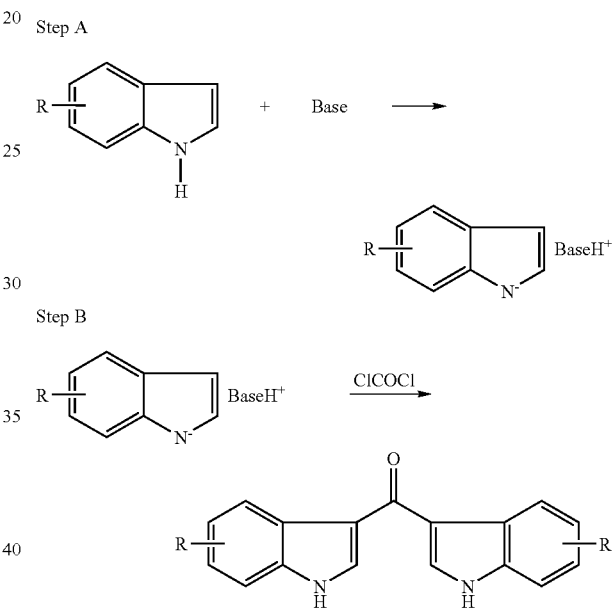

Step B

Step A
Preparation of the Indole Salt and its Derivatives
Step B
Condensation Reaction for Preparing bis-indole and bis-indole Derivatives The salt from step A (1 mole) was dissolved in an anhydrous inert organic solvent (e.g. hydrochloride solvents, dioxan, THF, ethyl ether) and poured into a cold solution (from −15 to −50° C.) of phosgene (with organic solvents such as CH$_2$Cl$_2$, toluene, THF, ethyl ether). After 1 hour, the temperature was allowed to rise (to 0–50° C.) and the solution was maintained at this temperature for another 10–24 hours. At the end of this period, the reaction mixture was filtered and the liquid concentrated. The solid thus obtained was subjected to purification on a silica gel chromatography column, obtaining the condensation product.

EXAMPLE 7/1

Preparation of 1,1-diindol-3-yl-oxomethane (ST 1463)

The magnesium salt of indole (2.43 g, 11 mmol) (obtained with the procedure described by Casiraghi G. et al., Tetrahedron 1992, 48 (27), 5619) was dissolved in 12 ml of CH$_2$Cl$_2$ and then poured into a solution of phosgene in 20% toluene (6.2 ml) and CH$_2$Cl$_2$ (10 ml). The reaction mixture was left at +5° C. for 16 hours. The organic phase was separated from the solid by filtration and concentrated to dryness. The resulting solid, after purification on a silica gel column, using ethyl acetate:hexane 6:4 as the mobile phase, yielded the diindol-oxomethane derivative as a yellow solid. Yield 90%.

C$_{17}$H$_{12}$N$_2$O (260.29); melting point=decomposes at 300° C.; Rf=0.54 (hexane/ethyl acetate 4:6); $^1$H (DMSO-D6) δ=8.36–8.24 (2H, d, CH aromatic); 8.20 (2H, s, CH indole); 7.90 (2H, br, NH); 7.60–7.50 (2H, d, CH aromatic); 7.30–7.10 (4H, m, CH aromatic). MS (IS) M$^-$=259. Elemental analysis: calculated C, 77.84; H, 5.38; N, 10.68. found C, 77.79; H, 5.02; N, 10.62.

EXAMPLE 8

The compound in example 8 was prepared using synthesis in Scheme 8 here below, according to the procedures described by Diez-Barra E. et al., Synth Commun 1993, 23(13), 1783.

Scheme 8

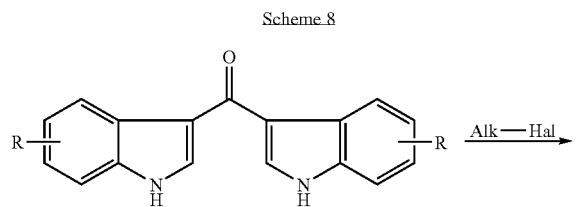

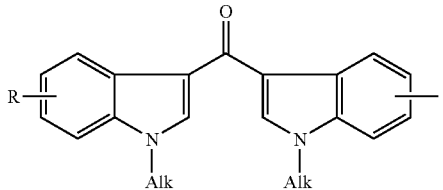

Hal = Cl, Br

EXAMPLE 8/1

Preparation of di-(N-benzyl-indol-3-yl)-oxomethane (ST 1473)

The compound was prepared according to the procedure described by Diez-Barra E. et al., Synth Commun 1993, 23(13), 1783, starting from the product prepared as described in example 7/1.

A yellow solid was obtained. Yield 90%.

C$_{31}$H$_{24}$N$_2$O (440.54); melting point=decomposes at 305° C.; Rf=0.52 (hexane/ethyl acetate 7:3); $^1$H (DMSO-D$_6$) δ=8.50–8.48 (2H, m, CH aromatic); 8.40–8.30 (2H, m, CH aromatic); 7.60–7.50 (2H, m, CH aromatic); 7.42–7.20 (14H, m, CH aromatic, indole); 5.62–5.58 (4H, m, CH$_2$). MS (IS) M$^+$=441. Elemental analysis: calculated C, 84.51; H, 5.49; N, 6.35. found C, 84.19; H, 5.98; N, 6.29.

EXAMPLE 9

The compound in example 9 was prepared according to synthesis in Scheme 9 here below.

Scheme 9

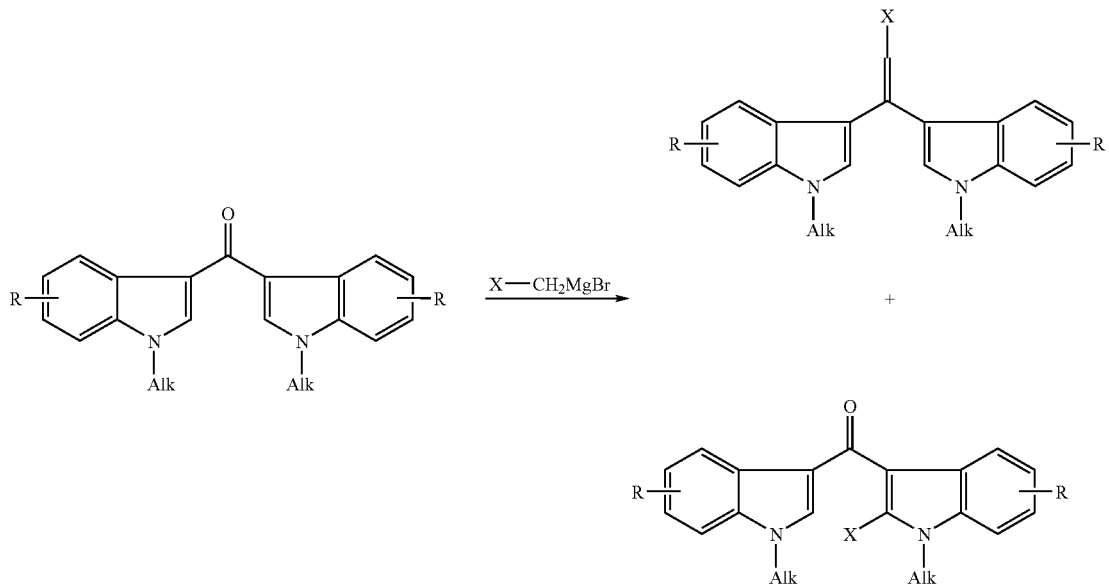

Alkylation and Alkylation/Dehydration of Oxomethane Derivatives

In an anhydrous solvent (e.g. THF, dioxane, ethyl ether) 1 mole of oxomethane derivative (prepared as described in example 8/1) was dissolved and the salt (e.g. lithium, magnesium, copper, phosphonium salt) of the alkyl one wishes to produce the derivative of was added at low temperature (from −50 to +10° C.), in excessive amounts in relation to the substrate (from 2 to 10 mol). On completing the addition, the temperature of the reaction mixture was allowed to rise to ambient temperature (22 to 30° C.). On completing the reaction, the solution was concentrated by vacuum evaporation of the solvent, and the semisolid thus obtained was diluted with $CH_2Cl_2$.

The solution was washed with water and then with a saturated solution of NaCl. The organic phase was concentrated again and the resulting solid was submitted to purification, obtaining the desired product.

EXAMPLE 9/1

Preparation of 1,1-di-(N-benzyl-indol-3-yl)-1-butene and -(N-benzyl-indol-3-yl, N-benzyl-2-propyl indol-3-yl)-oxomethane (ST 1492 and ST 1494)

The compound described in example 8/1 (1 g, 2.3 mmol) was dissolved in anhydrous THF (13 ml) and the resulting solution was cooled to +5° C. Seven ml of a solution of propylmagnesium chloride 2M in ethyl ether were added. After 1 hour, 100 ml of $CH_2Cl_2$ and 50 ml of water were added. The organic phase was washed with a saturated solution of NaCl 100 ml before being concentrated to dryness. The crude reaction product thus obtained was subjected to chromatography on silica gel, eluting with a mixture of hexane:ethyl acetate 8:2. In this way, the end compounds were isolated and purified from the crude reaction product (yields of both compounds 10%).

(ST1492) $C_{34}H_{30}N_2$(466.63); melting point=decomposes at 240° C.; Rf=0.31 (hexane/ethyl acetate 9:1); $^1H$ (DMSO-$D_6$) δ=7.60–6.80 (20H, m, CH aromatic, indole); 6.20–6.00 (1H, t, CH-); 5.42 (2H, s, $CH_2$); 5.30 (2H, s, $CH_2$); 2.24–2.18 (2H, q, $CH_2$); 1.10–1.00 (3H, t, $CH_3$). MS (IS) $M^-$=465. Elemental analysis: calculated C, 87.51; H, 6.48; N, 6.00. found C, 87.74; H, 6.48; N, 5.79.

(ST1494) $C_{34}H_{30}N_2O$ (482.63); melting point=Decomposes at 325° C.; Rf=0.68 (hexane/ethyl acetate 7:3); $^1H$ (DMSO-$D_6$) δ=8.20–8.10 (1H, m, CH aromatic, indole); 8.00 (1H, s, CH); 7.70–6.60 (1H, m, CH); 7.40–7.00 (16 H, m, aromatic, indole); 5.60 (2H, s, $CH_2$); 5.50 (2H, s, $CH_2$); 3.00–2.90 (2H, q, $CH_2$); 1.60–1.40 (2H, m, $CH_2$); 0.90–0.80 (3H, t, $CH_3$). MS (IS) $M^-$=465. Elemental analysis: calculated C, 84.61; H, 6.26; N, 5.80. found C, 84.54; H, 6.38; N, 5.69.

EXAMPLE 10

The compound in example 10 was prepared using synthesis in Scheme 10 here below.

Scheme 10

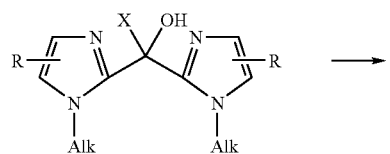

-continued

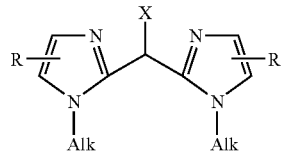

EXAMPLE 10/1

Preparation of phenyl-di-(1-N-benzyl-imidazol-2-yl)-methane (ST 1447)

0.84 g (2 mmol) of the compound prepared as described in example 6/1 were dissolved in 12 ml of HCOOH together with 2 g of carbon and the resulting mixture was heated under reflux for 24 hours. At the end of this period, the solution was cooled and diluted with 50 ml of MeOH, filtered on celite and then concentrated to dryness. The end product was separated from the crude reaction product by chromatography on silica gel (elution solvent hexane:ethyl acetate 7:3). Yield 40%.

$C_{27}H_{24}N_4$(404.51); melting point=decomposes at >200° C.; Rf=0.66 (hexane/ethyl acetate 7:3); $^1H$ (DMSO-$D_6$) δ=8.30–8.20 (4H, m, CH aromatic); 7.80–7.70 (2H, m, CH aromatic); 7.68–7.50 (4H, m, CH aromatic and imid.); 7.40–7.20 (10H, m, CH aromatic, imid. and CH); 5.70–5.60 (4H, m, $CH_2$). MS (IS) $M^-$=403. Elemental analysis: calculated C, 80.16; H, 5.98; N, 13.85. found C, 80.10; H, 5.89; N, 13.54.

EXAMPLE 11

The compounds in example 11 were prepared according to the procedure described by Diez-Barra E. et al., Synth Commun 1993, 23(13), 1783.

EXAMPLE 11/1

Preparation of 1,1-di-(N-benzyl-indol-3-yl)-butane (ST 1442)

ST 1385 1,1-di-indol-3-yl-butane, 290 mg (1 mmol), was thoroughly mixed and blended with potassium tertbutylate (280 mg) and tetrabutylammonium bromide (20 mg). The mixture thus obtained was held under ultrasonic stirring at ambient temperature. 640 mg (5 mmol) of benzylchloride at 0° C. were then added and the ultrasonic stirring was continued for 2 hours at room temperature. At the end of this period, the reaction mixture was treated with $H_2O/CHCl_3$; the chloroform phase was separated, washed with a small amount of water, dried on $Na_2SO_4$, filtered and concentrated to dryness. The end product was isolated and purified chromatographically on silica gel, eluting with hexane:ethyl ether 95:5.351 mg of product were obtained with a 78% yield.

$C_{34}H_{32}N_2$ (468); melting point=decomposes at >210° C.; Rf=0.53 (hexane/ether=8/2); $^1H$ (CDCl$_3$) δ=7.55 (2H, d, CH aromatic); 7.16–7.05 (10H, mm, CH aromatic); 7.04–6.88 (12H, mm, CH aromatic); 5.22 (4H, s, $CH_2$ aromatic); 4.42 (1H, t, CH); 2.13 (2H, q, $CH_2$); 1.40–1.23 (2H, m, $CH_2$) 0.98 (3H, t, $CH_3$). MS (IS) $M^-$=467. Elemental analysis: calculated C, 87.13; H, 6.88; N, 5.17. found C, 86.83; H, 7.04; N, 4.99.

EXAMPLE 11/2

Preparation of 1,1-di-(N-methyl-indol-3-yl)-butane (ST 1534)

The title compound was prepared using exactly the same procedure described in example 11/1, starting from ST 1385 and methyl iodide. Yield 84%.

$C_{22}H_{24}N_2$(316); melting point=decomposes at >200° C.; Rf=0.45 (hexane/AcOEt=9/1); $^1$H (CDCl$_3$) δ=7.29 (2H, d, CH aromatic); 7.24 (2H, d, CH aromatic); 7.21 (2H, t, CH aromatic); 7.08 (2H, t, CH aromatic); 6.88(2H, s, CH aromatic); 4.52 (1H, s, CH); 3.72 (6H, s, CH$_3$); 2.22 (2H, q, CH$_2$); 1.56–1.39 (2H, m, CH$_2$); 0.99 (3H, t, CH$_3$). MS (IS) M$^-$=315. Elemental analysis: calculated C, 83.50; H, 7.64; N, 8.85. found C, 82.98; H, 7.49; N, 8.72.

EXAMPLE 11/3

Preparation of 5,5-bis-(1-methyl-1H-indol-3-yl)-1 Pentanol (ST 1974)

The title compound was prepared using exactly the same procedure described in example 11/1 starting from ST 1346 and methyl iodide. Yield 75%.

$C_{23}H_{26}N_2O$ (346.47); Rf=0.25 (hexane/AcOEt 7:3); $^1$H(CDCl$_3$): δ=7.62 (2H, d, CH aromatic); 7.35–7.15 (4H, m, CH+CH aromatic); 7.12–6.98 (2H, m, CH aromatic); 6.85 (2H, s, CH aromatic); 4.60 (1H, t, CH); 3.75 (6H, s, N—CH$_3$); 3.65 (2H, t, CH$_2$O); 2.35–2.16 (2H, m, CH$_2$); 1.76–1.58 (2H, m, CH$_2$); 1.58–1.39 (2H, m, CH$_2$). MS (IS) M$^-$=345. AU calculated C 79.73; H 7.56; N 8.08. found C 79.61; H 7.49; N 8.01.

EXAMPLE 12

The compounds in example 12 were prepared using the procedure described by Angyal S. J., Beveridge R. J. Carbohydr. Res. 1978, 65, 229.

EXAMPLE 12/1

Preparation of (2S)-2,3-dihydroxy-1,1-diindol-3-yl-propane (ST 1331)

The title compound was obtained with a yield of 95% using the method described by Angyal S. J., Beveridge R. J. Carbohydr. Res. 1978, 65, 229, starting from the compound prepared as described in example 3/1.

$C_{19}H_{18}N_2O_2$ (306.4); melting point=decomposes at 200° C.; (α)$_D$=+38.50 (0.5% CH$_3$OH); Rf=0.5 (ethyl acetate); $^1$H (CDCl$_3$) δ=8.00 (2H, br, NH); 7.62–7.48 (2H, dd, CH aromatic); 7.26–7.20 (2H, m, CH aromatic); 7.20–6.86 (6H, m, CH aromatic); 4.64 (1H, d, CH); 4.60–4.20 (1H, d CH); 3.80–3.26 (2H, dd, CH); 1.80 (2H, br. OH). MS (IS) M$^-$=305. Elemental analysis: calculated (4% H$_2$O, 2.7% ethyl ether) C, 72.03; H, 6.60; N, 8.81. found C, 72.51; H, 6.47; N, 7.75.

EXAMPLE 12/2

Preparation of 1,1-di-indol-3-yl-1-deoxy-D-mannitol (ST 13491)

The title compound was obtained using the procedure described by Angyal S. J., Beveridge R. J. Carbohydr. Res. 1978, 65, 229, starting from the compound of example 1 step A. Yield 84%.

$C_{22}H_{24}N_2O_5$(396); melting point=decomposes at 60° C.; (α)$_D$=−38.6 (0.07% in CH$_3$OH); Rf=0.5 (CHCl$_3$/CH$_3$OH=7/3); $^1$H (DMSO-D$_6$) δ=10.60–10.70 (2H, br-s, NH); 7.50 (2H, t, CH aromatic); 7.25 (2H, d, CH aromatic); 7.13 (2H, s, CH aromatic); 6.90 (2H, m, CH aromatic); 6.80 (2H, m, CH aromatic); 5.00 (1H, br-s, CH); 4.00–4.40 (5H, m, OH); 3.30–3.60 (6H, m, CH$_2$). MS (IS) M$^-$=395. Elemental analysis: calculated (3% H$_2$O) C, 65.18; H, 6.20; N, 6.87. found C, 65.00; H, 6.40; N, 6.35.

EXAMPLE 13

The compounds in example 13 were prepared using the procedure described by Sainbury M., Hogan I. T. Synthesis 1984, 4, 872.

EXAMPLE 13/1

Preparation of 1,3-diacetoxy-2,2-(diindol-3-yl)-propane (ST 1370)

The title compound was obtained starting from the compound of example 2/8 according to the procedure decribed by Sainbury M., Hogan I. T. Synthesis 1984, 4, 872, doubling the moles of Ac$_2$O and AcONa. Yield 70%.

$C_{23}H_{22}N_2O_4$(390.4); melting point=183°–185° C.; Rf=0.78 (ethyl ether); $^1$H (CDCl$_3$) δ=8.10 (2H, s, NH); 7.32–7.24 (2H, d, CH aromatic); 7.22–7.16 (2H, m, CH aromatic); 7.14–7.08 (2H, d, CH aromatic); 7.04–6.98 (2H, t, CH aromatic); 6.80–6.64 (2H, t, CH aromatic; 4.84 (4H, s, CH$_2$); 1.90 (6H, s, CH$_3$). MS (IS) M$^-$=390. Elemental analysis: calculated C, 70.75; H, 5.68; N, 7.17. found C, 70.50; H, 5.35; N, 6.83.

EXAMPLE 13/2

Preparation of 5-acetoxy-1,1-diindol-3-yl-pentane (ST 1371)

The title compound was obtained using the method described by Sainbury M., Hogan I. T. Synthesis 1984, 4, 872, starting from the compound of example 2/4. Yield 80%.

$C_{23}H_{24}N_2O_2$(360.4); melting point=decomposes at >200° C.; Rf=0.42 (ethyl ether/hexane 7:3); $^1$H (CDCl$_3$) δ=7.80 (2H, br, NH); 7.62–7.48 (2H, dd, CH aromatic); 7.24–7.20 (2H, d, CH aromatic); 7.16–7.10 (2H, m, CH aromatic); 7.00–6.86 (4H, m, CH aromatic); 4.42–4.40 (1H, t, CH); 4.00–3.84 (2H, t, CH$_2$); 2.22–1.86 (2H, m, CH$_2$); 1.90 (3H, s, CH$_3$); 1.80–1.60 (2H, m, CH$_2$); 1.50–1.40 (2H, m, CH$_2$). MS (IS) M$^+$=361. Elemental analysis: calculated C, 76.57; H, 6.65; N, 7.77. found C, 76.27; H, 6.78; N, 7.25.

EXAMPLE 13/3

Preparation of 1,1-di-indol-3-yl-1-deoxy-pentaacetyl-D-glucose (ST 1363)

The title compound was obtained starting from the compound of example 2/10 according to the method described by Sainbury M., Hogan I. T. Synthesis 1984, 4, 872, using a 10-fold excess of Ac$_2$O and AcONa. Yield 70%.

$C_{32}H_{34}N_2O10$(606.1); melting point=190° C.;(α)$_D$=−23.8° (0.4% CHCl$_3$); Rf=0.8 (CHCl$_3$/CH$_3$OH 9:1); $^1$H (CDCl$_3$) δ=8.00 (2H, s, NH); 7.70–7.60 (2H, m, CH aromatic); 7.30–7.05 (4H, m, CH aromatic); 7.04–6.90 (4H, m, CH aromatic); 5.80–5.70 (1H, t, CH); 5.40–5.20 (2H, m, CH); 5.0 (2H, m, CH); 4.00–3.80 (2H, m, CH); 2.10 (3H, s, CH$_3$); 2.00 (3H, s, CH$_3$); 1.82 (3H, s, CH$_3$); 1.68 (3H, s, Ac); 1.64 (3H, s, Ac). MS (IS) M$^-$=605. Elemental analysis: calculated (3.4% H$_2$O) C, 65.18; H, 6.20; N, 6.87. found C, 65.10; H, 6.23; N, 6.40.

EXAMPLE 14

Preparation of 1,1-di-(indol-3-yl)-5-mesyloxy-pentane (ST 14881).

The title compound was obtained using the procedure described by Kim, J. H.; Yang, M. et al., J. Chem. Soc. Perkin. Trans. 1; 1998, (17), 2877–2880, starting from the compound of example 2/4. Yield 60%.

$C_{22}H_{24}N_2O_3S$ (396); melting point=decomposes at >200° C.; Rf=0.18 (Et$_2$O/hexane=6:4); $^1$H (CDCl$_3$) δ=7.90 (2H, s, NH); 7.3–7.5 (2H, d, CH aromatic); 6.95–7.10 (2H, t, CH aromatic); 6.90 (1H, s, CH aromatic); 4.20 (1H, t, CH); 2.80 (3H, s, CH$_3$S); 1.60–2.40 (8H, m, CH$_2$). MS (IS) M$^-$=395. Elemental analysis: calculated C, 66.66; H, 6.06; N, 7.07. found C, 66.54; H, 6.24; N, 6.98.

EXAMPLE 15

The compounds in example 15 were prepared using the procedure described by Tao, M. et al., Bioorg. Med. Chem. Lett. 1996, 6 (24), 3009.

EXAMPLE 15/1

Preparation of phenyl, hydroxy, di-(imidazol-2-yl)-methane (ST 1441)

A mixture consisting of 4.20 g (10 mmol) of the compound in example 6/1 and 1 g of Pd(OH)$_2$ in 200 ml of methanol was submitted to hydrogenation with H$_2$ at pressure (60 p.s.i.). The hydrogenation reaction was conducted at ambient temperature for 16 hours.

At the end of this period, the Pd was removed by filtration and the solution concentrated; the resulting solid was subjected to purification. The end product was isolated and purified chromatographically on silica gel (mobile phase AcOEt:MeOH 1:1). Yield 98%.

$C_{13}H_{12}N_4$ (240.26); melting point=decomposes at 200° C.; Rf=0.65 (AcOEt/MeOH/NH$_3$ 90:10:0.2); $^1$H (DMSO-D$_6$) δ=12.10–11.80 (2H, broad, NH); 7.40–7.34 (3H, m, CH aromatic); 7.30–7.14 (4H, m, CH imid.) 7.20–6.8 (4H, m, CH aromatic, OH). MS (IS) M$^+$=241. Elemental analysis: calculated C, 64.98; H, 5.03; N, 23.32. found C, 64.36; H, 5.23; N, 23.00.

EXAMPLE 15/2

Preparation of 1,1-di-(5-amino-indol-3-yl)-butane. 2HCl (ST 1437)

ST 1429, 1,1-di-(5-nitroindol-3-yl)-butane, 250 mg (0.66 mmol), was hydrogenated at 15 p.s.i. with 100 mg of 5% Pd/c in an ethanol solution in the presence of 2 ml of 15% HCl in absolute ethanol. After 4 hours the reduction was complete; the solution was filtered, concentrated to a small volume and acetone was then added under stirring. The product precipitated and was then vacuum filtered and dried. 216 mg of clean product were obtained with a yield of 84%.

$C_{20}H_{22}N_4$. 2HCl (391); melting point=decomposes at 248–243° C.; Rf=0.62 (CH$_3$CN/EtOH=6:4); $^1$H (DMSO-D$_6$) δ=11.95 (2H, br, NH); 10.50 (4H, br, NH$_2$); 7.55 (2H, s, CH aromatic); 7.50–7.25 (3H, m, CH aromatic); 7.10–6.90 (2H, m, CH aromatic); 4.35 (1H, t, CH); 2.15(2H, q, CH$_2$); 1.40–1.15 (2H, m, CH$_2$); 0.90 (3H, t, CH$_3$ aliphatic). MS (IS) M$^+$=319. Elemental analysis: calculated C, 61.38; H, 6.18; N, 14.31; C, 118.11. found C, 61.08; H, 6.25; N, 14.02; C, 118.48.

EXAMPLE 16

The compounds in example 16 were prepared using the procedure described by Smith, S. O. et al., J. Org. Chem. 1997, 62 (11), 3638.

EXAMPLE 16/1

Preparation of 1,1-(diindol-3-yl)-5-fluoro-pentane (ST 1381)

The compound of example 2/4 (318 mg; 1 mmol) was dissolved in CH$_2$Cl$_2$ (20 ml). To the solution held at 25° C. was added DAST (200 μl; 1.5 mmol) and the mixture was left to react for 30 minutes.

At the end of this period, a solution of 10% NaHCO$_3$ 10 ml) and CH$_2$Cl$_2$ (10 ml) was added to the reaction mixture. The organic phase was separated, dried with Na$_2$SO$_4$ and concentrated until a solid was obtained. The product was isolated and purifed by HPLC using a reverse-phase preparatory column (RP-18 column, mobile phase CH$_3$CN:H$_2$O 60:40). Yield 15%.

$C_{21}H_{20}N_2$ (300); melting point=206–208° C.; Rf=0.78 (hexane/iPrOH=9/1); $^1$H (DMSO-D$_6$) δ=10.40–10.80 (2H, br-s, NH); 7.52 (1H, d, CH aromatic); 7.45 (1H, m, CH aromatic); 7.37 (1H, d, CH aromatic); 7.20 (1H, m, CH aromatic); 7.07 (1H, t, CH); 6.95 (2H, m, CH); 6.68 (1H, s, CH); 4.65 (1H, br-s, CH); 2.75–3.00 (2H, m, CH$_2$); 1.95–2.40 (2H, m, CH$_2$); 1.90–1.60 (2H, m, CH$_2$); 1.70 (2H, m, CH$_2$). MS (IS) M$^-$=299. Elemental analysis: calculated C, 84.00; H, 6.66; N, 9.33. found C, 84.19; H, 6.50; N, 9.03.

EXAMPLE 16/2

Preparation of (R,S)-5-fluoro-1,1-(indol-2-yl indol-3-yl)-pentane (ST 1421)

The compound in example 2/12 (318 mg; 1 mmol) was dissolved in CH$_2$Cl$_2$ (20 ml). To the solution held at 25° C. was added DAST (200 μl; 1.5 mmol) and the mixture was left to react for 30 minutes.

At the end of this period, a solution of 10% NaHCO$_3$ (10 ml) and CH$_2$Cl$_2$ (10 ml) was added to the reaction mixture. The organic phase was separated, dried with Na$_2$SO$_4$ and concentrated until a solid was obtained. The product was isolated and purified by HPLC using a reverse-phase preparatory column (RP-18 column, mobile phase CH3CN:H$_2$O 60:40). Yield 15%.

$C_{21}H_{21}FN_2$(320); melting point=77–81° C.; Rf=0.44 (hexane/iPrOH=85/15); $^1$H (CH$_3$CN) δ=9.00–8.80 (2H, br-s, NH); 7.40 (4H, m, CH aromatic); 7.30 (1H, br-s, CH); 6.95 (4H, m, CH aromatic); 6.60 (1H, s, H3'b); 4.65 (1H, t, CH); 4.50–4.75 (2H, t, CH$_2$); 2.20 (2H, m, CH$_2$); 1.70–1.80 (2H, m, CH$_2$); 1.40 (2H, m, CH$_2$). MS (IS) M$^-$=319. Elemental analysis: calculated C, 78.75; H, 6.56; F, 5.93; N, 8.75. found C, 78.85; H, 6.70; F, 5.90; N, 8.94.

EXAMPLE 17

Preparation of bis-[1,1-di-(N-carbonyl-indol-3-yl)-butane](ST 1533)

ST 1385, 580 mg (2 mmol), and 500 mg of carbonyl-diimidazole (3 mmol) were dissolved in 10 ml of anhydrous dimethylsulphoxide. The reaction was held at 125° C. for 2 hours under stirring. At the end of this period, the reaction mixture was cooled and 200 ml of iced H$_2$O were added slowly. The product precipitated and was filtered, washed on the filter with iced water and then crystallised with methanol. 520 mg of the title compound were obtained. Yield 82.7%.

The product consisted in a mixture of two stereoisomers, one with the two butyric chains in the trans position (65%) and the other in the cis position (35%).

$C_{21}H_{14}N_2S_2$(358.5); melting point=178° C.; Rf=0.41 (hexane/dioxane 8:2) $^1$H (DMSO-$D_6$) δ=7.80–7.70 (3H, m, CH aromatic); 7.60–7.40 (5H, m, CH aromatic); 7.40–7.20 (3H, m, CH aromatic); 7.20–7.00 (3H, m, CH aromatic, CH). MS (IS) $M^+$ (—$H_2O$)=359. Elemental analysis: calculated C, 70.36; H, 3.93; N, 7.81. found C, 70.10; H, 3.85; N, 7.49.

EXAMPLE 18

Preparation of 3-(5-bromo-1-(1H-indol-3-yl)-pentyl)-1H-indole (ST 1880)

The title compound was prepared using the procedure described by Campbell, J. A. et al., J. Org. Chem. 1996, 61(18), 6313–6325, starting from ST 1346.

ST 1346, 318 mg (1 mmol) was dissolved in 20 ml of anhydrous $CH_2Cl_2$; the solution was cooled to −5° C. and first 904 mg of triphenyl phosphine (4 mmol) and then 1,324 g of tetrabromo-methane (4 mmol) were added slowly in succession. The reaction mixture was left at −5° C. for 42 hours, and then, when the reaction was completed, concentrated to, complete dryness. The residue was chromatographed on an $SiO_2$ column using hexane:ethyl acetate 8:2 as the eluent. 297 mg of clean product were obtained with a yield of 78%

$C_{21}H_{21}BrN_2$ (381.32); Rf=0.68 (hexane/AcOEt=6:4); $^1$H(CDCl$_3$): δ=7.86 (2H, br-s, —NH); 7.66 (2H, d, CH aromatic); 7.34 (2H, d, CH aromatic); 7.27–7.16 (2H, m, CH aromatic); 7.16–7.03 (2H, m, CH aromatic); 6.37 (2H, s, CH aromatic); 4.53 (1H, t, CH); 3.40 (2H, t, $CH_2Br$); 2.37–2.19 (2H, m, $CH_2$); 2.05–1.97 (2H, m, $CH_2$); 1.71–1.49 (2H, m, $CH_2$). MS (IS) $M^-$=380. Elemental analysis: calculated C 66.15; H 5.55; Br 20.95; N 7.35. found C 66.28; H 5.51; Br 20.64; N 7.29.

EXAMPLE 19

Preparation of 4-(5,5-di-(1H-indol-3-yl)-pentyl)-2-morpholinyl-methyl ether (ST 1860)

The title compound was prepared according to the procedure described by Dutta, A. K. et al.; J. Med. Chem., 1996, 39 (3), 749–756, starting from ST 1880 and 2-methoxy-morpholin prepared as described by Caviraghi, G. et al., J. Heterocy Chem, 18, 825 (1981).

ST 1880, 381 mg (1 mmol), 2-methoxy-morpholin 234 mg (2 mmol), and $K_2CO_3$ 690 mg (5 mmol), finely ground, were thoroughly mixed with 5 ml of anhydrous DMA and heated with stirring at 80° C. for 5 hours. At the end of this period, 30 ml of $H_2O$ were added and extraction was performed with ethyl acetate (3×50 ml). The organic phases were pooled, washed with a small amount of water, dried on anhydrous $Na_2SO_4$ and concentrated to dryness. The residue was purified on an $SiO_2$ chromatography column using a gradient of hexane:ethyl acetate ranging from 7:3 to 4:6 160 mg of product were obtained (yield 38%).

$C_{26}H_{31}N_3O_2$ (417.55) Rf=0.19 (hexane/AcOEt=6:4); $^1$H(CDCl$_3$): δ=7.93 (2H, br-s, —NH); 7.55 (2H, d, CH aromatic); 7.32 (2H, d, CH aromatic); 7.19–7.07 (2H, m, CH aromatic); 7.06–6.93 (4H, m, 2 CH aromatic); 4.60 (1H, t, CH morph.); 4.45 (1H, t, CH gem.); 4.02–3.89 (1H, m, CH morph.); 3.72–3.58 (1H, m, CH morph.); 3.42 (3H, s, $CH_3$); 2.52–2.43 (2H, m, $CH_2$); 2.42–2.28 (2H, m, $CH_2$ morph.); 2.28–2.15 (2H, m, $CH_2$); 1.82–1.47 (4H, m, CH2 e CH2 morph.) 1.47–1.35 (2H, m, $CH_2$). MS (IS) $M^-$=416. Elemental analysis: calculated: C 74.79; H 7.48; N 10.06. found C, 74.98; H 7.36; N 9.93.

EXAMPLE 20

Cytotoxicity Test on Sensitive Tumour Cell Lines

This test was used to evaluate the survival of the human cell lines MCF-7 (human mammary carcinoma), LoVo (human colon adenocarcinoma), and MES-SA (human uterine sarcoma). The tumour cells were incubated with the compound, at scalar concentrations, (500 μM÷0.97 μM) for 24 hours; the compound was then removed and cell survival was evaluated after 48 hours using the sulforodamine B test (J. Natl. Cancer Inst. 82, 1107–1112). The antiproliferative activity of the compounds was evaluated in terms of the $IC_{50}$ (concentration of the molecule that inhibits 50% of cell survival) processed with a curve-fitting program (Am. J. Physiol. 1978., 235, E97–E102) and expressed as μM±S.D.

The compounds tested and the results obtained are reported in Tables 1, 2 and 3 here below.

TABLE 1

(Antiproliferative activity on MCF-7 cell line)

| ST[a] | TEST COMPOUND[b] | MCF-7[c] |
|---|---|---|
| 1363 | 1,1-di-indol-3-yl-1 deoxy-pentaacetyl-D-glucose | 25 ± 2.8 |
| 1371 | 5-acetoxy-1,1-diindol-3-yl-pentane | 27.7 ± 4.2 |
| 1382 | 1,1-(diindol-3-yl)-5-fluoro-pentane | 28.5 ± 6 |
| 1385 | 1,1-di-(indol-3-yl)-butane | 27 ± 3.2 |
| 1393 | 1,1-di-(5-hydroxy-indol-3-yl)-butane | 5.9 ± 0.8 |
| 1421 | (R,S)-5-fluoro-1,1-(indol-2-yl,indol-3-yl)-pentane | 20.4 ± 2.8 |
| 1422 | 5-hydroxy-1,1-di(5,6-methylenedioxy-indol-3-yl)-pentane | 43.1 ± 1.2 |
| 1429 | 1,1-di-(5-nitro-indol-3-yl)-butane | 10.4 ± 0.3 |
| 1431 | di-(5-ethoxycarbonyl-pyrrol-2-yl)-phenyl-methane | 20.3 ± 1.4 |
| 1437 | 1,1-di-(5-amino-indol-3-yl)-butane dihydrochloride | 8.3 ± 1.2 |
| 1438 | 1,1-di-(5-fluoro-indol-3-yl)-butane | 28.1 ± 0.9 |
| 1440 | Phenyl,hydroxy,di(N,N-dibenzyl-imidazol-2-yl)-methane | 17 ± 2.9 |
| 1477 | 1,1-di-(5-acetamido-indol-3-yl)-butane | 33.1 ± 2.9 |
| 1478 | 1,1-di-(5,6-methylenedioxy-indol-3-yl)-butane | 11.8 ± 0.4 |
| 1487 | 1,1-di-(indol-3-yl)-cyclohexyl methane | 29.9 ± 0.006 |
| 1488 | 1,1-di-(indol-3-yl)-5-mesyloxy-pentane | 13.4 ± 2.2 |
| 1625 | (R,S)-1,1-(indol-2-yl,indol-3-yl)-butane | 13.4 ± 1 |
| 1730 | 4-hydroxy-1,1-di-(5,6-methylenedioxy-indol-3-yl)-butane | 24.5 ± 3.7 |
| 1731 | (R,S)-4-hydroxy-1,1-(5,6-methylenedioxy-indol-2-yl, 5,6-methylenedioxy-indol-3-yl)-butane | 30.1 ± 4 |

[a]identification code of test compound.
[b]chemical name of test compound.
[c]antiproliferative activity value expressed as $IC_{50}$ (μM ± S.D.).

TABLE 2

(Antiproliferative activity on Mes-Sa cell line)

| ST[a] | TEST COMPOUND[b] | Mes-Sa[c] |
|---|---|---|
| 1363 | 1,1-di-indol-3-yl-1-deoxy-pentaacetyl-D-glucose | 33.6 ± 5.9 |
| 1371 | 5-acetoxy-1,1-diindol-3-yl-pentane | nd |
| 1382 | 1,1-(diindol-3-yl)-5-fluoro-pentane | 40.2 ± 4.1 |
| 1385 | 1,1-di-(indol-3-yl)-butane | 19.5 ± 4.0 |

TABLE 2-continued (Antiproliferative activity on Mes-Sa cell line)

| ST[a] | TEST COMPOUND[b] | Mes-Sa[c] |
|---|---|---|
| 1393 | 1,1-di-(5-hydroxy-indol-3-yl)-butane | 5.7 ± 0.1 |
| 1421 | (R,S)-5-fluoro-1,1-(indol-2-yl,indol-3-yl)-pentane | nd |
| 1422 | 5-hydroxy-1,1-di-(5,6-methylenedioxy-indol-3-yl)-pentane | 79.3 ± 7.8 |
| 1429 | 1,1-di-(5-nitro-indol-3-yl)-butane | 15 ± 2.5 |
| 1431 | di-(5-ethoxycarbonyl-pyrrol-2-yl)-phenyl-methane | nd |
| 1437 | 1,1-di-(5-amino-indol-3-yl)-butane dihydrochloride | 4.4 ± 0.06 |
| 1438 | 1,1-di-(5-fluoro-indol-3-yl)-butane | 21.8 ± 4.4 |
| 1440 | phenyl,hydroxy,di-(N,N-dibenzyl-imidazol-2-yl)-methane | 4.7 ± 0.4 |
| 1477 | 1,1-di-(5-acetamido-indol-3-yl)-butane | 28.7 ± 0.2 |
| 1478 | 1,1-di-(5,6-methylenedioxy-indol-3-yl)-butane | 17 ± 2 |
| 1487 | 1,1-di-(indol-3-yl)-cyclohexyl-methane | 38.7 ± 0.03 |
| 1488 | 1,1-di-(indol-3-yl)-5-mesyloxy-pentane | 15.8 ± 1.8 |
| 1625 | (R,S)-1,1-(indol-2-yl,indol-3-yl)-butane | 14.1 ± 3.8 |
| 1730 | 4-hydroxy-1,1-di-(5,6-methylenedioxy-indol-3-yl)-butane | nd |
| 1731 | (R,S)-4-hydroxy-1,1-(5,6-methylenedioxy-indol-2-yl, 5,6-methylenedioxy-indol-3-yl)-butane | nd |

[a]identification code of test compound.
[b]chemical name of test compound.
[c]antiproliferative activity value expressed as IC$_{50}$ (μM ± S.D.).
nd = not determined.

TABLE 3

(Antiproliferative activity on LoVo cell line)

| ST[a] | TEST COMPOUND[b] | Lovo[c] |
|---|---|---|
| 1363 | 1,1-di-indol-3-yl-1 deoxy-pentaacetyl-D-glucose | 31.3 ± 1.6 |
| 1371 | 5-acetoxy-1,1-diindol-3-yl-pentane | 33 ± 3 |
| 1382 | 1,1-(diindol-3-yl)-5-fluoro-pentane | 33.5 ± 3.7 |
| 1385 | 1,1-di-(indol-3-yl)-butane | 26.4 ± 0.4 |
| 1393 | 1,1-di-(5-hydroxy-indol-3-yl)-butane | 3.0 ± 0.5 |
| 1421 | (R,S)-5-fluoro-1,1-(indol-2-yl,indol-3-yl)-pentane | 20.7 ± 0.7 |
| 1422 | 5-hydroxy-1,1-di-(5,6-methylenedioxy-indol-3-yl)-pentane | 23 ± 4.4 |
| 1429 | 1,1-di-(5-nitro-indol-3-yl)-butane | 23.6 ± 0.5 |
| 1431 | di-(5-ethoxycarbonyl-pyrrol-2-yl)-Phenyl-methane | 35.6 ± 0.5 |
| 1437 | 1,1-di-(5-amino-indol-3-yl)-butane dihydrochloride | 16.7 ± 3.4 |
| 1438 | 1,1-di-(5-fluoro-indol-3-yl) -butane | 20 ± 0.8 |
| 1440 | phenyl,hydroxy,di-(N,N-dibenzyl-imidazol-2-yl)-methane | 11.7 ± 0.2 |
| 1477 | 1,1-di-(5-acetamido-indol-3-yl)-butane | 59.4 ± 6.9 |
| 1478 | 1,1-di-(5,6-methylenedioxy-indol-3-yl)-butane | 15.4 ± 1.8 |
| 1487 | 1,1-di-(indol-3-yl)-cyclohexyl-methane | 24.9 ± 0.1 |
| 1488 | 1,1-di-(indol-3-yl)-5-mesyloxy-pentane | 11 ± 1.6 |
| 1625 | (R,S)-1,1-(indol-2-yl,indol-3-yl)-butane | 17.1 ± 3.8 |
| 1730 | 4-hydroxy-1,1-di-(5,6-methylenedioxy-indol-3-yl)-butane | 9.3 ± 0.9 |
| 1731 | (R,S)-4-hydroxy-1,1-(5,6-methylenedioxy-indol-2-yl, 5,6-methylenedioxy-indol-3-yl)-butane | 23.9 ± 0.7 |

[a]identification code of test compound.
[b]chemical name of test compound.
[c]antiproliferative activity value expressed as IC$_{50}$ (μM ± S.D.).

EXAMPLE 21

Cytotoxicity Test on Resistant Tumour Cell Lines

This test was used to evaluate the survival of human cell lines resistant to doxorubicin (about 100 times) and cross-resistant to daunorubicin, actinomycin D, mitoxantrone, vincristine, vinblastin, taxol, colchicine, and etoposide.

The following cell lines were used: MCF-7-Dx (human mammary carcinoma), LoVo-Dx (human colon adenocarcinoma), MES-SA Dx (human uterine sarcoma).

The compounds tested are given in Tables 4, 5 and 6. Before using the association doxorubicin-tested compound, the cytotoxicity of the cells was evaluated with the tested compound (alone) as follows: the cells were incubated with the compound, at scalar concentrations (500 μM÷0.97 μM), for 24 hours; the compound was then removed and cell survival was evaluated after 48 hours with the above-mentioned sulforodamine B test. The antiproliferative activity of the compounds was evaluated in terms of IC$_{50}$ (concentration of the compound that inhibits 50% of cell survival) processed with the above-mentioned curve-fitting program.

The curves were then plotted for doxorubicin alone and for doxorubicin in the presence of the tested compound at a non-toxic concentration (IC$\leq$90).

The IC$_{50}$ values reported in Tables 4, 5 and 6 show the degree of potentiation of doxorubicin activity induced by the compound (MDR ratio).

TABLE 4

(Chemosensitising activity on MCF-7 Dx cell line)

| | | MCF-7 DX[f] | |
|---|---|---|---|
| ST[d] | TEST COMPOUND[e] | IC$_{50}$ (μM) | MDR ratio |
| 1339 | 2,3-5,6-di-O-isopropylidene-1,1-di-indol-3-il-1-deoxy-D-mannitol | 98.2 ± 12 | 3.2/1.0 = 3.2*** (IC0 = 20); 3.6/1.6 = 2.2*** (ICO = 10) |
| 1350 | 1,1-di-indol-3-yl-1-deoxy-D-glucose | 70.8 ± 3.7 | 6.6/1.6 = 4.1*** (IC2 = 50); 7.2/3.6 = 2.0** (IC0 = 25) |
| 1353 | 2,3-5,6-di-O-isopropylidene-1,1-di-7-azaindol-3-yl-1-deoxy-D-mannitol | >500 | 6.5/1.0 = 6.5*** (IC17 = 500) |
| 1363 | 1,1-di-indol-3-yl-1-deoxy-pentaacetyl-D-glucose | 65.4 ± 0.7 | 5.8/1.9 = 3** (IC6 = 20) |
| 1371 | 5-acetoxy-1,1-diindol-3-yl-pentane | 74.1 ± 2.5 | 11.1/2.6 = 4.3*** (IC0 = 30); 5.5/2.5 = 2.2**** (IC5 = 40) |
| 1382 | 1,1-(diindol-3-yl)-5-fluoro-pentane | 40.2 ± 3 | 6.1/3.6 = 1.7* (IC4 = 10); 7.4/1.9 = 3.8*** (IC9 = 20) |
| 1385 | 1,1-di-(indol-3-il)-butano | 34.6 ± 2.0 | 3.9/1.9= 2.0** (IC2 = 20) 4.4/4.3 = 1.0 (IC0 = 10) |
| 1393 | 1,1-di-(5-hydroxy-indol-3-yl)-butane | 9.2 ± 0.4 | 5.3/4.5 = 1.1 (IC0 = 4) 6.1/4.6 = 1.3 (IC0 = 2) |
| 1422 | 5-hydroxy-1,1-di(5,6-methylenedioxy-indol-3-yl)-pentane | 40.1 ± 1.2 (IC3 = 20) | 7.8/4.6 = 1.7 3.3/3.2 = 1 IC7 = 10 |
| 1429 | 1,1-di-(5-nitro-indol-3-yl)-butane | 12.9 ± 0.7 | nd |
| 1437 | 1,1-di-(5-amino-indol-3-yl)-butane dihydrochloride | 28.6 ± 5.5 18.4 ± 1.4 | nd |
| 1438 | 1,1-di-(5-fluoro-indol-3-yl)-butane | 41.8 ± 5.3 | 10.7/3.5 = 3* (IC1 = 20) |

TABLE 4-continued (Chemosensitising activity on MCF-7 Dx cell line)

| ST[d] | TEST COMPOUND[e] | MCF-7 DX[f] IC$_{50}$ (μM) | MDR ratio |
|---|---|---|---|
| 1440 | phenyl,hydroxy,di-(N,N-dibenzyl-imidazol-2-yl)-methane | 29.7 ± 2.6 | 14.2/5.6 = 2.5 (IC8 = 10) 1.8/1.3 = 1.4 |
| 1473 | di-(N-benzyl-indol-3-yl)-oxomethane | >500 | 3.4/1.1 = 3.2* (IC19 = 50) |
| 1478 | 1,1-di-(5,6-methylenedioxy-indol-3-yl)-butane | 15.2 ± 1.9 | 9.4/4.5 = 2.1* (IC0 = 2) |
| 1487 | 1,1-di-(indol-3-yl)-cyclohexyl-methane | 15.3 ± 1 | nd |
| 1488 | 1,1-di-(indol-3-yl)-5-mesyloxy-pentane | 9.7 ± 1.3 | 7.1/1.2 = 5.7** (IC0 = 4) 2.6/4 = 0.65 (IC0 = 4) |
| 1492 | 1,1-di-(N-benzyl-indol-3-yl)-1-butene | >500 117 ± 7 | 8/0.8 = 9.6**** (IC5 = 50) 1.5/0.51 = 3*** (IC0 = 10) 2.4/0.3 = 7.1*** (IC0 = 5) |
| 1494 | di-(N-benzil-indol-3-yl,N-benzyl-2-propyl-indol-3-yl)-oxomethane | >200 | 2.1/0.17 = 12.2*** (IC10 = 50) 0.9/0.28 = 3.1* (IC8 = 5) 1.2/0.37 = 3.3** (IC3 = 10) |

[d]identification code of test compound.
[e]chemical name of test compound.
[f]chemosensitising activity value expressed as MDR ratio calculated as follows: IC$_{50}$ doxorubicin/IC$_{50}$ doxorubicin combined with the tested compound at a subtoxic concentration.
$P < 0.05$, $P < 0.01$, *$P < 0.001$, ****$P < 0.0001$ are the P values calculated with the curve-fitting program described above in order to compare the doxorubicin curves in the presence and absence of the tested compound.
Indicated in brackets is the subtoxic μM concentration of the product used for calculating MDR ratio.
The left-hand column gives the IC$_{50}$ values for the tested compound alone expressed in μM ± SD; in the processing of the IC$_{50}$, the value of the subtoxic concentration IC ≦ 20 of the tested compound is also evaluated.

TABLE 5

(Chemosensitising activity on Mes-Sa Dx cell line)

| ST[d] | TEST COMPOUND[e] | Mes-Sa Dx[f] IC$_{50}$ (μM) | MDR ratio |
|---|---|---|---|
| 1339 | 2,3-5,6-di-O-isopropylidene-1,1-di-indol-3-yl-1-deoxy-D-mannitol | 56.1 ± 11 | nd |
| 1350 | 1,1-di-indol-3-yl-1-deoxy-D-glucose | 81.4 ± 8.0 | 2.4/1.4 = 1.7* (IC0 = 50) |
| 1353 | 2,3-5,6-di-O-isopropylidene-1,1-di-7-azaindol-3-yl-1-deoxy-D-mannitol | nd | nd |
| 1363 | 1,1-di-indol-3-yl-1-deoxy-pentaacetyl-D-glucose | nd | nd |
| 1371 | 5-acetoxy-1,1-diindol-3-yl-pentane | 53 ± 0.4 | nd |
| 1382 | 1,1-(diindol-3-yl)-5-fluoro-pentane | 12.45 ± 0.3 | 0.7/0.9 = 0.82 (IC20 = 5) |
| 1385 | 1,1-di-(indol-3-yl)-butane | 33.6 ± 2.9 | nd |
| 1393 | 1,1-di-(5-hydroxy-indol-3-yl)-butane | 7.5 ± 0.3 | 3.03/2.2 = 1.4* (IC7 = 3) |
| 1422 | 5-hydroxy-1,1-di-(5,6-methylenedioxy-indol-3-yl)-pentane | 73.3 ± 2.7 | 1.8/1.8 = 1 (IC3 = 15) |
| 1429 | 1,1-di-(5-nitro-indol-3-yl)-butane | 15.3 ± 0.4 | 3.4/0.8 = 4.3*** (IC0 = 10) |
| 1437 | 1,1-di-(5-amino-indol-3-yl)-butane dihydrochloride | 12.2 ± 0.8 | 2.8/2.4 = 1.2 (IC5 = 5) 3.2/2.4 = 1.3 (IC5 = 2.5) |
| 1438 | 1,1-di-(5-fluoro-indol-3-yl)-butane | 35.6 ± 1.7 | 2.6/2.2 = 1.2 (IC20 = 20) 2.1/3.2 = 0.7 (IC0 = 10) |
| 1440 | phenyl,hydroxy,di-(N,N-dibenzyl-imidazol-2-yl)-methane | 14.9 ± 2.5 | 6/2.2 = 2.8** (IC8 = 5) |
| 1473 | di-(N-benzil-indol-3-yl)-oxomethane | >500 | nd |
| 1478 | 1,1-di-(5,6-methylenedioxy-indol-3-yl)-butane | 7.8 ± 1.5 | 1.2/1.5 = 0.8 (IC3 = 2) |
| 1487 | 1,1-di-(indol-3-yl)-cyclohexyl-methane | 16 ± 3.5 | 1.3/1.6 = 0.8 (IC11 = 4) |
| 1488 | 1,1-di-(indol-3-yl)-5-mesyloxy-pentane | 10.3 ± 1.9 | 0.95/0.72 = 1.3 (IC15 = 5) |

TABLE 5-continued (Chemosensitising activity on Mes-Sa Dx cell line)

| ST[d] | TEST COMPOUND[e] | Mes-Sa Dx[f] IC$_{50}$ (μM) | MDR ratio |
|---|---|---|---|
| 1492 | 1,1-di-(N-benzyl-indol-3-yl)-1-butene | 178.3 ± 41 | nd |
| 1494 | di-(N-benzil-indol-3-yl, N-benzyl-2-propyl-indol-3-yl)-oxomethane | >200 | nd |

[d] identification code of test compound.
[e] chemical name of test compound.
[f] chemosensitising activity value expressed as MDR ratio calculated as follows: IC$_{50}$ doxorubicin/IC$_{50}$ doxorubicin combined with the tested compound at a subtoxic concentration.
$P < 0.05$, $P < 0.01$, $*P < 0.001$, $****P < 0.0001$ are the P values calculated with the curve-fitting program described above in order to compare the doxorubicin curves in the presence and absence of the tested compound.
Indicated in brackets is the subtoxic μM concentration of the product used for calculating MDR ratio.
The left-hand column gives the IC$_{50}$ for the tested compound alone expressed in μM ± SD; in the processing of the IC$_{50}$, the value of the subtoxic concentration IC ≦ 20 of the tested compound is also evaluated.

TABLE 6

(Chemosensitising activity on LoVoDx cell line)

| ST[d] | TEST COMPOUND[e] | Lovo Dx[f] IC$_{50}$ (μM) | MDR ratio |
|---|---|---|---|
| 1339 | 2,3-5,6-di-O-isopropylidene-1,1-di-indol-3-yl-1-deoxy-D-mannitol | 11 ± 0.6 | 3.8/1.4 = 2.8*** (IC9 = 4) 3.5/1.8 = 2** (IC15 = 8) |
| 1350 | 1,1-di-indol-3-il-1-deossi-D-glucose | >500 | nd |
| 1353 | 2,3-5,6-di-O-isopropylidene-1,1-di-7-azaindol-3-yl-1-deoxy-D-mannitol | 367 ± 82 | nd |
| 1363 | 1,1-di-indol-3-yl-1-deoxy-pentaacetyl-D-glucose | 121 ± 12 | nd |
| 1371 | 5-acetoxy-1,1-diindol-3-yl-pentane | 47.9 ± 4.7 | 1.93/1.95 = 0.98 (IC0 = 15) |
| 1382 | 1,1-(diindol-3-yl)-5-fluoro-pentane | 34.3 ± 6.9 | 2.2/2.6 = 0.9 (IC16 = 20) 3.4/5.4 = 0.6 (IC0 = 10) |
| 1385 | 1,1-di-(indol-3-yl)-butane | 17.6 ± 0.9 | 2.7/1.4 = 1.9 (IC14 = 10) 1.4/2.8 = 0.5 (IC31 = 5) |
| 1393 | 1,1-di-(5-hydroxy-indol-3-yl)-butane | 2.7 ± 0.4 | 3.4/1.75 = 1.95 (IC7 = 0.5) |
| 1422 | 5-hydroxy-1,1-di-(5,6-methylenedioxy-indol-3-yl)-pentane | 22.3 ± 2.9 | 1.8/2.1 = 0.9 (IC11 = 15) 4.2/1.7 = 2.4 (IC0 = 7.5) |
| 1429 | 1,1-di-(5-nitro-indol-3-yl)-butane | 10.2 ± 0.5 | 2.6/1.2 = 2.1* (IC0 = 5) 2.4/2.2 = 1.1 (IC14 = 2.5) |
| 1437 | 1,1-di-(5-amino-indol-3-yl)-butane dihydrochloride | 8 ± 0.6 | 4.7/4.1 = 1.2 (IC14 = 2) |
| 1438 | 1,1-di-(5-fluoro-indol-3-yl)-butane | 25.9 ± 3.1 | 5/9.2 = 0.5 (IC0 = 10) |
| 1440 | phenyl,hydroxy,di-(N,N-dibenzyl-imidazol-2-yl)-methane | 4.6 ± 0.6 | 5.6/14.9 = 0.4 (IC0 = 2) |
| 1473 | di-(N-benzyl-indol-3-yl)-oxomethane | 8.6 ± 2.9 | 3.7/1.2 = 3.1 (IC0 = 0.5) |
| 1478 | 1,1-di-(5,6-methylenedioxy-indol-3-yl)-butane | 10.7 ± 0.6 | 2.3/2.8 = 0.8 (IC19 = 4) |
| 1487 | 1,1-di-(indol-3-yl)-cyclohexyl-methane | 27.8 ± 2.1 | 2.2/1.3 = 1.7* (IC0 = 2) |
| 1488 | 1,1-di-(indol-3-yl)-5-mesyloxy-pentane | 18.1 ± 0.6 | 3.8/3.2 = 1.2 (IC15 = 3.5) |
| 1492 | 1,1-di-(N-benzyl-indol-3-yl)-1-butene | >350 | 1.8/0.4 = 4.4*** (IC9 = 50) 1.82/0.49 = 3.7** (IC2 = 25) |
| 1494 | di-(N-benzyl-indol-3-yl,N-benzyl-2-propyl-indol-3-il)-oxomethane | >200 | 2.2/0.12 = 18*** (IC5 = 50) |

[d] identification code of test compound.
[e] chemical name of test compound.
[f] chemosensitising activity value expressed as MDR ratio calculated as follows: IC$_{50}$ doxorubicin/IC$_{50}$ doxorubicin combined with the tested compound at a subtoxic concentration.
$P < 0.05$, $P < 0.01$, $*P < 0.001$, $****P < 0.0001$ are the P values calculated with the curve-fitting program described above in order to compare the doxorubicin curves in the presence and absence of the tested compound.
Indicated in brackets is the subtoxic μM concentration of the product used for calculating MDR ratio.
The left-hand column gives the IC$_{50}$ for the test compound alone expressed in μM ± SD; in the processing of the IC$_{50}$, the value of the subtoxic concentration IC ≦ 20 of the tested compound is also evaluated.

EXAMPLE 22

Chemosensitising Effect on All-Trans Retinoic Acid (ATRA) on Acute Promyelocytic Leukaemia Cells ATRA is a potent inducer of terminal differentiation in acute promyelocytic leukaemia (APL).

Clinical studies have demonstrated that the treatment of APL patients with ATRA induces an increase in survival and in event-free survival (EFS) (Blood 72(2): 567–72, 1988; Blood 76: 1704–09, 1990; N. Engl. J. Med. 324(20): 1385–93, 1991; Blood 78(6): 1413–19, 1991).

The administration of therapeutic doses of ATRA ($10^{-6}$ M) induces dermatotoxic- and hepatotoxic-type reactions (ATRA syndrome) in treated patients (Blood 76: 260a (abstr. Suppl), 1990; Ann. Intern. Med. 117(4): 292–96, 1992).

Experiment were performed in order to verify the possibility of using ATRA at lower doses, obtaining a reduction in side effects caused by this compound, while maintaining the same therapeutic efficacy.

To achieve this end, a number of compounds according to the invention described herein were used, and their ability to enhance the sensitivity of ATRA and potentiate its antiproliferative, cell-differentiative and apoptogenic effects on a number of leukaemia cell lines was studied.

In the experiments conducted, reported here below, two APL cell lines were used.

The first line used was the NB4 cell line, bearing the t(15;17) chromosomal translocation which generates the fusion protein PML/RARα. This line is very sensitive to the differentiative action of pharmacological doses of ATRA ($10^{-7}$–$10^{-6}$ M).

The second line used was the HL60 cell line which responds to ATRA (but is less sensitive than the NB4 cell line). This cell line does not present the above-mentioned chromosomal translocation.

The HL60 and NB4 cells were seeded at a density of 150,000 cells/ml in RPMI 1640 medium containing 10% foetal calf serum, and were treated with the tested compounds in the presence and absence of suboptimal doses of ATRA (5–10 nM for NB4 and 0.5 μM for HL60, respectively) in the dark, and returned to the incubator for 3 days without ever replacing the culture medium.

The maximum ATRA-induced differentiative effect is normally observed on the 3rd to 4th days of treatment, concomitantly with a significant growth arrest.

Control cultures were treated with DMSO at the same concentrations used to dilute the tested compounds and ATRA, in that this vehicle is itself differentiating in particular experimental conditions.

Evaluation of Cell Differentiation by Assay of Reduction of Nitr Blue Tetrazolium (NBT)

To analyse the differentiative effect of the tested compounds vs ATRA, on the third day of treatment 500,000 viable cells were harvested from each sample, centrifuged for 10 minutes at 1.000 rpm and resuspended in 1 ml of RPMI 1640 medium containing 10% foetal calf serum, 1 mg/ml of nitroblue tetrazolium (NBT) and 100 ng of PMA (phorbol 12-myristate 13-acetate).

The cells thus resuspended were incubated in the dark at 37° C. for 60 minutes.

At the end of the incubation, the cell suspension was centrifuged for 10 minutes at 10,000 rpm; the pellet obtained was then resuspended in 1 ml of PBS containing 10% Triton X-100 and sonicated to lysis.

Spectrophotometric readings of the samples were then taken at a wavelength of 540 nm: samples containing differentiated cells shifted towards a violet colour, whereas control samples and/or samples with non-differentiated cells were colourless or, at any rate, much less intensely coloured.

Flow Cytofluorimetric Analysis of Cell Cycle

To assess the effect of the tested compounds on the various phases of the cell cycle, on the third day of treatment 500,000 cells were harvested, centrifuged at 1,000 rpm for 10 minutes, washed twice in PBS w/o (PBS without calcium and magnesium) and fixed in a solution of 50% PBS w/o+50% methanol/acetone (1:4 v/v) for at least 1 hour; the cells were then centrifuged as described, washed in PBS w/o and centrifuged again.

200 μl of propidium iodide 100 μg/ml and 200 μl of RNase 150 kU/mg were then added to the cell pellet.

After a 30-min incubation in the dark at room temperature, the samples were analysed by flow cytofluirometry.

EXAMPLE 22/1

Differentiation of NB4 Cells Treated with 5-hydroxy-1,1-di-(indol-3-yl)-pentane (ST 1346) in Combination with Suboptimal Doses of ATRA In-vitro experiments, conducted on NB4 cells subjected to single or combined treatments with ST 1346 at doses of 1, 5, 10, and 50 μM and ATRA (0.5–0.01 μM) showed that the tested compound (ST 1346) was capable of substantially sensitising ATRA (administered at suboptimal doses) in inducing terminal differentiation, with reaching a maximal effect already at the dose of 10 μM.

The results obtained are given in FIG. 1 and show that the combined treatments yielded $AC_{50}$ values of 1.5±0.5 μM; (fold induction: 3.0)

The $AC_{50}$ (Activating Concentration) is the concentration at which the tested compound induces 50% of cell differentiation.

Fold Induction is the increase in the differentiation value of the cell sample treated with the tested compound +ATRA vs the value of the cell sample treated with ATRA alone. This value provides an indication of the ability (potency) of the tested compound to enhance ATRA induced cell differentiation.

EXAMPLE 22/2

Evaluation of the Effect of ST 1346 in the Presence and Absence of ATRA on the Cell Cycle of NB4 Cell Line The effects of single or combined treatments with ST 1346 at doses of 1, 5, 10, and 50 μM, and ATRA at suboptimal doses on the NB4 cell cycle were evaluated.

The results obtained show that high doses of the tested compound alone induce growth arrest (in the G0/G1 phase of the cell cycle) and apoptosis, whereas the combination of the compound according to the invention and ATRA gives rise to a dramatic (dose-dependent) growth arrest in the G0/G1 phase of the cycle, with induction of cell differentiation (FIG. 1).

The results obtained are given in Table 7.

It should be noted that when the compound according to the invention described herein was administered in combination with ATRA, even at the highest doses, it lost its apoptogenic effect.

TABLE 7

(Chemosensitising effects of ST1346 on ATRA on NB4 cell cycle)

| TREATMENT | G0/G1 | G2/M | S | APOPTOSIS |
|---|---|---|---|---|
| CONTROL | 46.2 | 12.3 | 41.5 | 18.5 |
| ST1346 1μM | 46.9 | 15.7 | 37.4 | 23 |
| ST1346 5 μM | 47.4 | 13.8 | 38.8 | 24 |
| ST1346 10 μM | 50.0 | 14.7 | 35.3 | 23 |
| ST1346 50 μM | 59.4 | 7.3 | 33.3 | 46 |
| ATRA 0.01 μM | 54.6 | 14.4 | 31.0 | 10 |
| ATRA 0.01 μM + ST1346 1 μM | 61.5 | 12.9 | 25.6 | 14 |
| ATRA 0.01 μM + ST1346 5 μM | 58.0 | 13.5 | 28.5 | 13.5 |
| ATRA 0.01 μM + ST1346 10 μM | 60.0 | 12.6 | 27.4 | 13 |
| ATRA 0.01 μM + ST1346 50 μM | 84.2 | 6.3 | 9.5 | 17 |

EXAMPLE 22/3

Effect of ST 1346 in the Presence and Absence of ATRA on Induction of Terminal Differentiation of HL60 Cells In this experiment, the effect of the compound according to the invention on induction of terminal differentiation of HL60 cells was evaluated.

A dose-response curve was plotted for ST 1346 at doses of 1, 5, 10, and 50 µM, in the presence or absence of suboptimal doses of ATRA, on HL60 cells.

Figure 2:
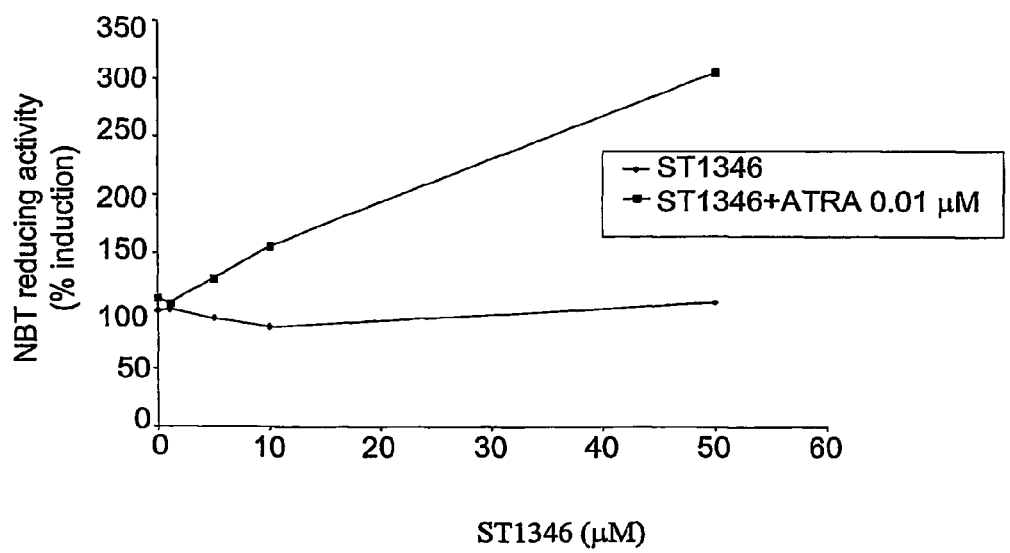

The results obtained are reported in FIG. 2 and show that the compound according to the invention is capable, in a dose-dependent manner, of substantially sensitising ATRA in inducing terminal cell differentiation of tumour cells with an $AC_{50}$ of 14.8±1.6 µM; fold induction: 2.7.

EXAMPLE 22/4

Evaluation of the Effect of 1,1-di(indol-3-yl)-4-hydroxybutane (ST 1707) in the Presence and Absence of ATRA on Differentiation and on NB4 Cell Cycle To evaluate the differentiation-enhancing activity of the tested compound, NB4 cells were treated with scalar doses of ST 1707 of 1, 5, 10, and 50 µM, in the presence or absence of suboptimal doses of ATRA.

Figure 3:
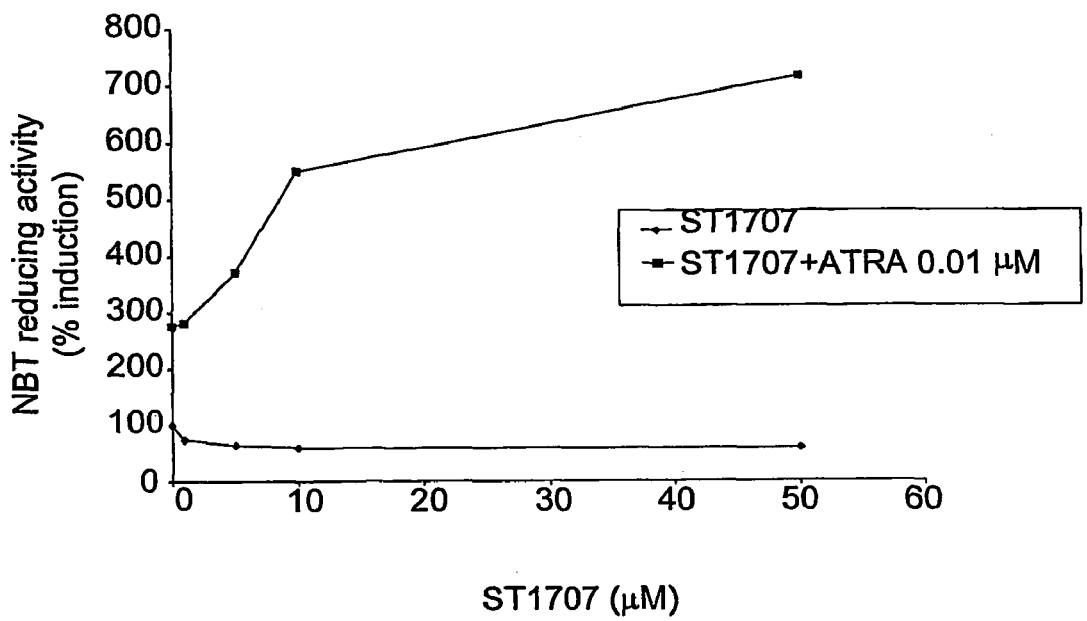

The results obtained are reported in FIG. 3 and show that the test compound is capable of significantly potentiating ATRA-induced terminal differentiation of leukaemia cells in a dose-dependent manner ($AC_{50}$: 8.3±0.05 µM; fold induction: 2.5).

The results obtained in cell cycle analysis are reported in Table 8 and show that the compound according to the invention, when administered alone, does not modify the percentage of cells present in the various phases of the cycle as compared to controls and does not induce apoptosis. When ST 1707 was administered in combination with ATRA, it induced a significant dose-dependent arrest of the cells in the G0/G1 phase of the cycle, as marker of cell differentiation.

TABLE 8

(Chemosensitising effects of ST1707 on ATRA on NB4 cell cycle)

| TREATMENT | G0/G1 | G2/M | S | APOPTOSIS |
|---|---|---|---|---|
| CONTROL | 52.9 | 9.6 | 37.5 | 20.5 |
| ST1707 1 µM | 51.7 | 10.1 | 38.2 | 17.0 |
| ST1707 5 µM | 52.5 | 11.1 | 36.4 | 19.5 |
| ST1707 10 µM | 52.2 | 10.8 | 37.0 | 17.5 |
| ST1707 50 µM | 52.0 | 12.0 | 36.0 | 17.0 |
| ATRA 0.01 µM | 65.0 | 11.0 | 24.0 | 17.5 |
| ATRA 0.01 µM + ST1707 1 µM | 65.4 | 11.8 | 22.8 | 17.0 |
| ATRA 0.01 µM + ST1707 5 µM | 69.8 | 11.3 | 18.9 | 14.0 |
| ATRA 0.01 µM + ST1707 10 µM | 70.4 | 11.5 | 18.1 | 13.0 |
| ATRA 0.01 µM + ST1707 50 µM | 80.6 | 9.0 | 10.4 | 11.5 |

EXAMPLE 22/5

Figure 4:
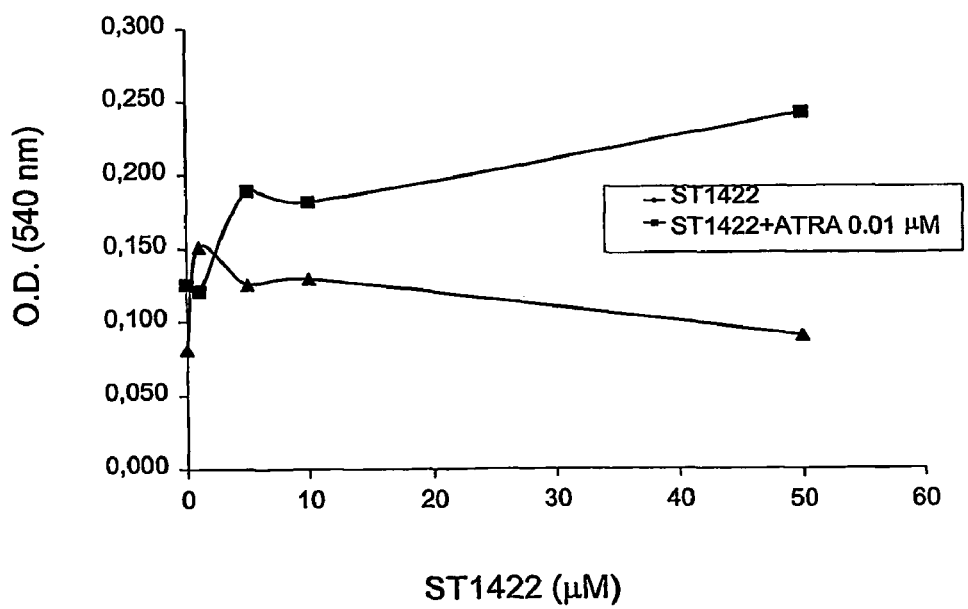

Evaluation of the Effect of 5-hydroxy-1,1-di-(5,6-methylenedioxy-indol-3-yl)-pentane (ST 1422) in the Presence and Absence of ATRA on the Induction of Terminal Differentiation of NB4 Cells In this experiment, the activity of ST 1422 on NB4 cells was evaluated at doses of 1, 5, 10, and 50 µM in the presence and absence of suboptimal doses of ATRA. The results obtained are reported in FIG. 4 and show that the above-mentioned NBT test revealed a marked sensitising effect of the tested compound in increasing ATRA induced terminal differentiation, with $AC_{50}$ values of 9.8±0.1 µM; fold induction: 1.85.

EXAMPLE 22/6

Figure 5:
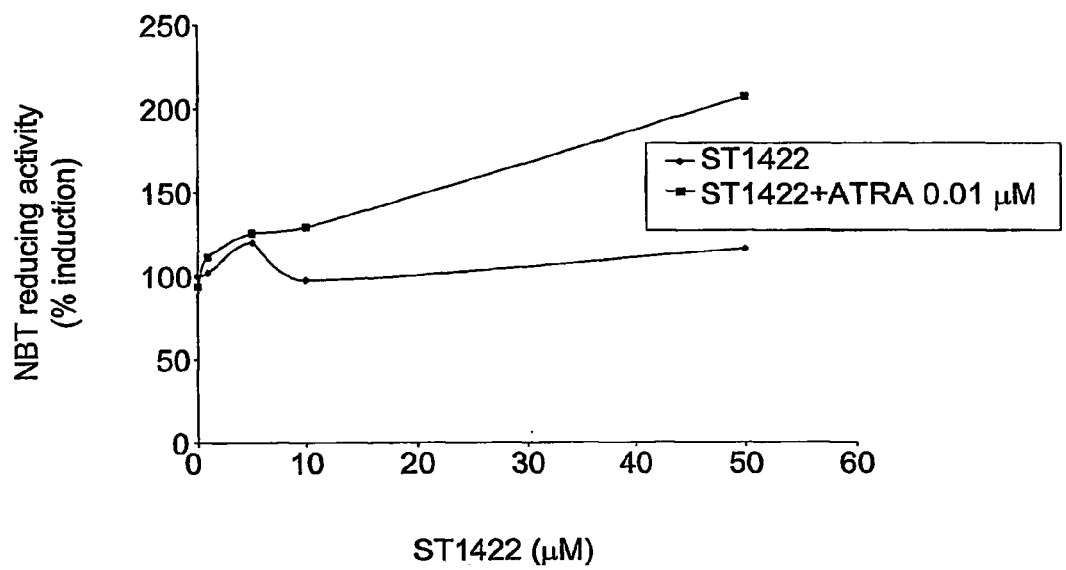

Evaluation of the Effect of 5-hydroxy-1,1-di-(5,6-methylenedioxy-indol-3-yl)-pentane (ST 1422) in the Presence and Absence of ATRA on Induction of Terminal Differentiation and on HL60 Cell Cycle In this experiment, the effect of ST 1422 was evaluated at doses of 1, 5, 10, and 50 µM, in the presence and absence of suboptimal doses of ATRA, on induction of terminal differentiation and on HL60 cell cycle. The results obtained are reported in FIG. 5 and show that the compound according to the invention was capable of inducing a fairly substantial sensitising effect on ATRA-induced terminal differentiation in the tumour cell line tested, with $AC_{50}$ values of 13.6±2.6 µM; fold induction: 2.2.

Moreover, the results obtained with cell cycle analysis reported in Table 9, show that, even in this case, the compound according to the invention was capable of inducing ATRA-mediated cell growth arrest in G0/G1 phase. The compound according to the invention, when tested alone, showed no effect on the induction of apoptosis.

TABLE 9

(Chemosensitising effects of ST1422 on ATRA on HL60 cell cycle)

| TREATMENT | G0/G1 | G2/M | S |
|---|---|---|---|
| CONTROL | 59.1 | 9.2 | 31.7 |
| ST1422 1 µM | 56.2 | 10.0 | 33.8 |
| ST1422 5 µM | 57.6 | 10.4 | 32.0 |
| ST1422 10 µM | 57.8 | 10.5 | 31.7 |
| ST1422 50 µM | 65.8 | 16.4 | 17.8 |
| ATRA 0.5 µM | 63.3 | 11.0 | 25.7 |
| ATRA 0.5 µM + ST 1422 1 µM | 66.8 | 11.0 | 22.2 |
| ATRA 0.5 µM + ST 1422 5 µM | 65.1 | 11.4 | 23.5 |
| ATRA 0.5 µM + ST 1422 10 µM | 62.5 | 12.5 | 25.0 |
| ATRA 0.5 µM + ST 1422 50 µM | 75.7 | 13.8 | 10.5 |

EXAMPLE 22/7

Effect of 5,5-bis(1-methyl-1H-indol-3-yl)-1-pentanol (ST 1974) in the Presence and Absence of ATRA on NB4 Cells In this experiment, the effects of the compound according to the invention were evaluated at doses of 1, 5, 10, and 50 µM on NB4 cells in the presence and absence of suboptimal doses of ATRA.

Figure 6:
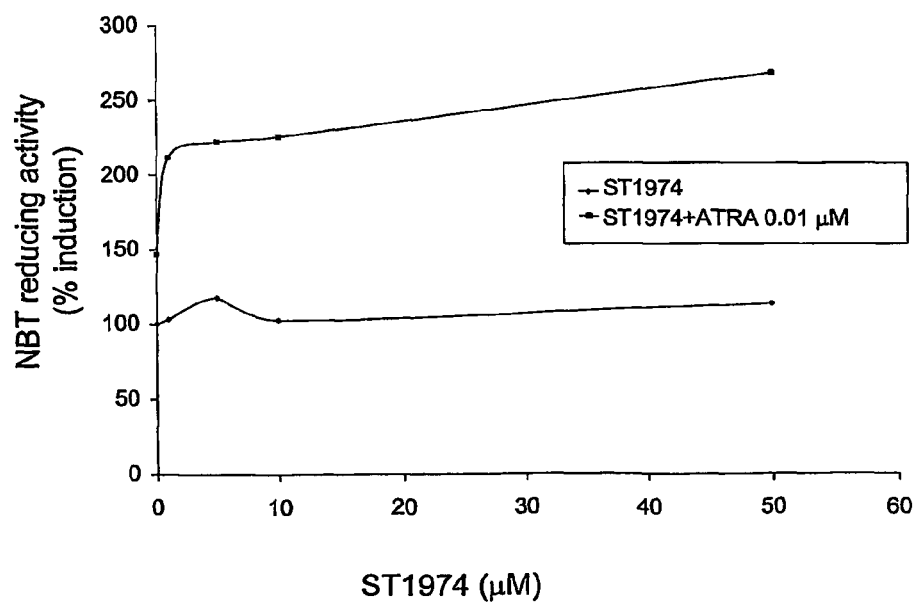

The results obtained, reported in FIG. 6, show that the compound according to the invention was capable of substantially increasing the differentiating effect of ATRA in a dose-dependent manner, with $AC_{50}$ values of 7.8±2.6 µM; fold induction: 1.8.

EXAMPLE 22/8

Effect of 5,5-bis(1-methyl-1H-indol-3-yl)-1-pentanol (ST 1974) in the Presence and Absence of ATRA on Induction of Terminal Differentiation and on HL60 Cell Cycle In this experiment, the effect of the compound according to the invention was evaluated at doses of 1, 5, 10, and 50 µM in the presence and absence of suboptimal doses of ATRA on the induction of terminal differentiation and on HL60 cell cycle.

Figure 7:
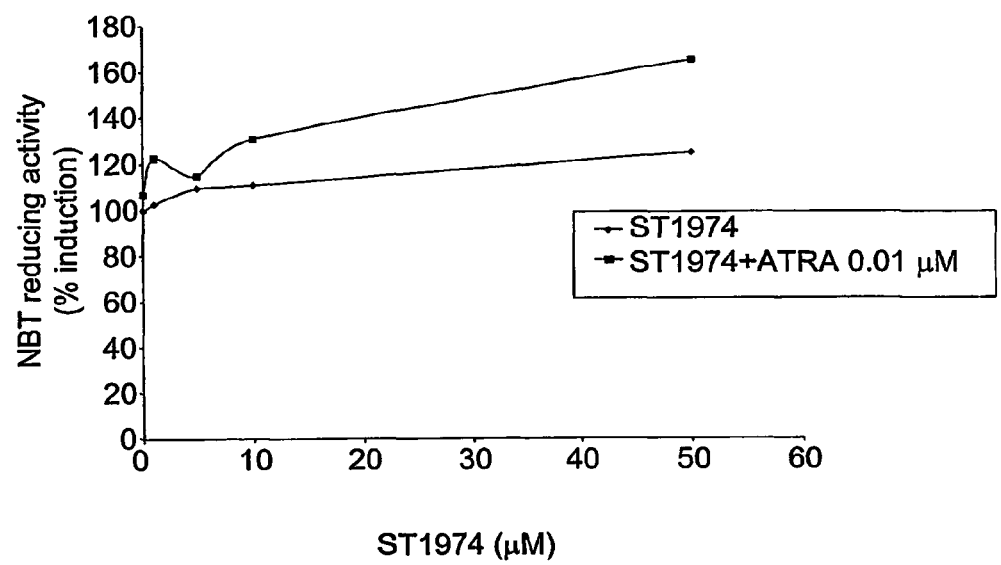

The results obtained are reported in FIG. 7 and show that the above-mentioned NBT test revealed a sensitising dose-dependent effect of the compound according to the invention on the ability of ATRA to induce terminal differentiation of HL60 cells, with $AC_{50}$ values of 9.5±2.6 µM; fold induction: 1.6.

When the compound according to the invention was administered in combination with ATRA, it induced a marked arrest of the cells in the G0/G1 phase of the cell cycle.

The results obtained are given in Table 10.

TABLE 10

(Chemosensitising effect of ST1974 on ATRA on HL60 cell cycle)

| TREATMENT | G0/G1 | G2/M | S |
|---|---|---|---|
| CONTROL | 59.1 | 9.2 | 31.7 |
| ST1974 1 µM | 58.9 | 11.1 | 30 |
| ST1974 5 µM | 59.3 | 11.4 | 29.3 |
| ST1974 10 µM | 57.8 | 12.2 | 30 |
| ST1974 50 µM | 67.7 | 12.3 | 20 |
| ATRA 0.5 µM | 63.4 | 11.0 | 25.6 |
| ATRA 0.5 µM + ST1974 1 µM | 62.0 | 11.7 | 26.3 |
| ATRA 0.5 µM + ST1974 5 µM | 63.8 | 10.5 | 25.7 |
| ATRA 0.5 µM + ST1974 10 µM | 65.4 | 10.5 | 24.1 |
| ATRA 0.5 µM + ST1974 50 µM | 81.8 | 10.6 | 7.6 |

EXAMPLE 22/9

Effect of 4,4-di-(1H-indol-3-yl)-butanoic Acid (ST 1961) in the Presence and Absence of ATRA on Induction of Terminal Differentiation and on NB4 Cell Cycle In this experiment, the effect of the compound according to the invention was evaluated at doses of 1, 5, 10, and 50 µM in the presence and absence of suboptimal doses of ATRA on the induction of terminal differentiation and on the NB4 cell cycle.

Figure 8:
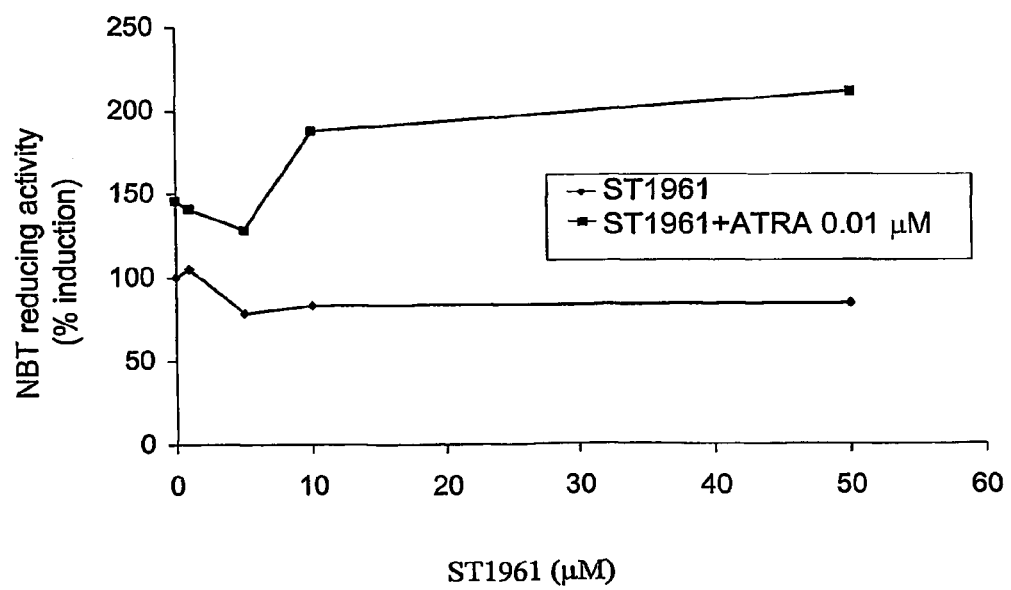

The results obtained are given in FIG. 8: the NTB test show that a sensitising effect of the compound according to the invention on the ability of ATRA to promote the induction of terminal differentiation was obtained, with an $AC_{50}$ of 6.6±2.0 µM; fold induction: 1.4.

In addition the results obtained with cell cycle analysis, reported in Table 11, show that, at high doses, the tested compound has a fairly substantial potentiating effect on ATRA activity in inducing the arrest of cells in the G0/G1 phase.

TABLE 11

(Effect of combination of ST1961 and ATRA on NB4 cell cycle)

| TREATMENT | G0/G1 | G2/M | S | APOPTOSIS |
|---|---|---|---|---|
| CONTROL | 45.5 | 14.5 | 40.0 | 22.0 |
| ST1961 1 µM | 47.5 | 15.6 | 36.9 | 18.5 |
| ST1961 5 µM | 49.7 | 13.0 | 37.3 | 24.0 |
| ST1961 10 µM | 48.4 | 14.1 | 37.5 | 24.0 |
| ST1961 50 µM | 56.3 | 14.0 | 29.7 | 24.0 |
| ATRA 0.01 µM | 55.8 | 17.3 | 26.9 | 12.5 |
| ATRA 0.01 µM + ST 1346 1 µM | 57.1 | 13.9 | 29.0 | 17.5 |
| ATRA 0.01 µM + ST 1346 5 µM | 58.4 | 13.9 | 27.7 | 17.0 |
| ATRA 0.01 µM + ST 1346 10 µM | 58.4 | 13.0 | 28.6 | 15.0 |
| ATRA 0.01 µM + ST 1346 50 µM | 82.2 | 8.0 | 9.8 | 10.0 |

The invention claimed is:
1. 1,1-di-(N-benzyl-indol-3-yl)-1-butene.
2. Pharmaceutical composition containing 1,1-di-(N-benzyl-indol-3-yl)-1-butene as an active ingredient, and at least one pharmaceutically acceptable excipient and/or diluent.

* * * * *